(12) United States Patent
Berglund

(10) Patent No.: US 12,194,253 B2
(45) Date of Patent: Jan. 14, 2025

(54) CATHETER ANCHOR APPARATUS AND METHODS

(71) Applicant: OpCare LLC, Charleston, SC (US)

(72) Inventor: David Nathan Berglund, Indian Trail, NC (US)

(73) Assignee: OpCare LLC, Charleston, SC (US)

( * ) Notice: Subject to any disclaimer, the term of this patent is extended or adjusted under 35 U.S.C. 154(b) by 0 days.

(21) Appl. No.: 18/032,102

(22) PCT Filed: Oct. 13, 2021

(86) PCT No.: PCT/US2021/054699
§ 371 (c)(1),
(2) Date: Apr. 14, 2023

(87) PCT Pub. No.: WO2022/081650
PCT Pub. Date: Apr. 21, 2022

(65) Prior Publication Data
US 2023/0321401 A1     Oct. 12, 2023

Related U.S. Application Data

(60) Provisional application No. 63/091,847, filed on Oct. 14, 2020.

(51) Int. Cl.
*A61M 25/02* (2006.01)
(52) U.S. Cl.
CPC ..... *A61M 25/02* (2013.01); *A61M 2025/0273* (2013.01)
(58) Field of Classification Search
CPC .......... A61M 25/02; A61M 2025/0273; A61M 2025/0246; A61M 2025/0266; A61M 2025/028; A61M 27/00; A61M 2005/1587; A61M 1/90; A61M 1/912; A61M 1/915; A61M 39/0247; A61M 35/006; A61M 39/10
See application file for complete search history.

(56) References Cited

U.S. PATENT DOCUMENTS

| | | | | |
|---|---|---|---|---|
| 4,397,641 | A | * | 8/1983 | Jacobs ................. A61M 25/02 D24/128 |
| 4,869,719 | A | * | 9/1989 | Hogan ................. A61M 25/02 604/174 |
| 5,116,324 | A | | 5/1992 | Brierley et al. |

(Continued)

OTHER PUBLICATIONS

International Search Report and Written Opinion for corresponding International App. No. PCT/US2021/054699.

*Primary Examiner* — Bradley J Osinski
(74) *Attorney, Agent, or Firm* — Nelson Mullins Riley & Scarborough LLP

(57) ABSTRACT

An anchor assembly for securing a catheter to a human body. An anchor assembly includes an anchor comprising an anchor body and a flange coupled with the anchor body. The flange has a top side and a bottom side opposite the top side, the bottom side configured to engage a human body. The anchor body defines at least one bore configured to receive a catheter therein. An adhesive dressing is disposed on the top side of the flange. The adhesive dressing includes a first portion and a second portion. The first portion at least partially covers the first side of the flange, and the second portion extends radially outward of the flange relative to the anchor body.

6 Claims, 23 Drawing Sheets

(56) References Cited

U.S. PATENT DOCUMENTS

| | | | |
|---|---|---|---|
| 5,232,453 A | | 8/1993 | Plass et al. |
| 5,833,666 A | * | 11/1998 | Davis .................... A61M 25/02 |
| | | | 128/DIG. 26 |
| 7,563,251 B2 | | 7/2009 | Bierman et al. |
| 8,877,061 B2 | | 11/2014 | Lovell |
| 2002/0165502 A1 | * | 11/2002 | Motisi ............... A61M 25/0075 |
| | | | 137/533.19 |
| 2006/0095008 A1 | | 5/2006 | Lampropoulos et al. |
| 2006/0129103 A1 | * | 6/2006 | Bierman ............... A61M 25/02 |
| | | | 604/174 |
| 2008/0004572 A1 | | 1/2008 | Morris et al. |
| 2008/0243082 A1 | | 10/2008 | Goodman |
| 2008/0269657 A1 | * | 10/2008 | Brenneman ............ A61B 46/10 |
| | | | 602/41 |
| 2011/0106014 A1 | * | 5/2011 | Helm, Jr. .............. A61M 25/02 |
| | | | 604/178 |
| 2013/0053785 A1 | * | 2/2013 | Parvatiyar ............. A61M 25/02 |
| | | | 604/174 |
| 2019/0030224 A1 | * | 1/2019 | Lin .................... A61F 13/00068 |
| 2019/0159939 A1 | * | 5/2019 | Coulthard ........... A61F 13/0216 |
| 2019/0160275 A1 | * | 5/2019 | Funk .................. A61M 39/1011 |
| 2020/0315655 A1 | * | 10/2020 | Bitner ................ A61B 17/3403 |

\* cited by examiner

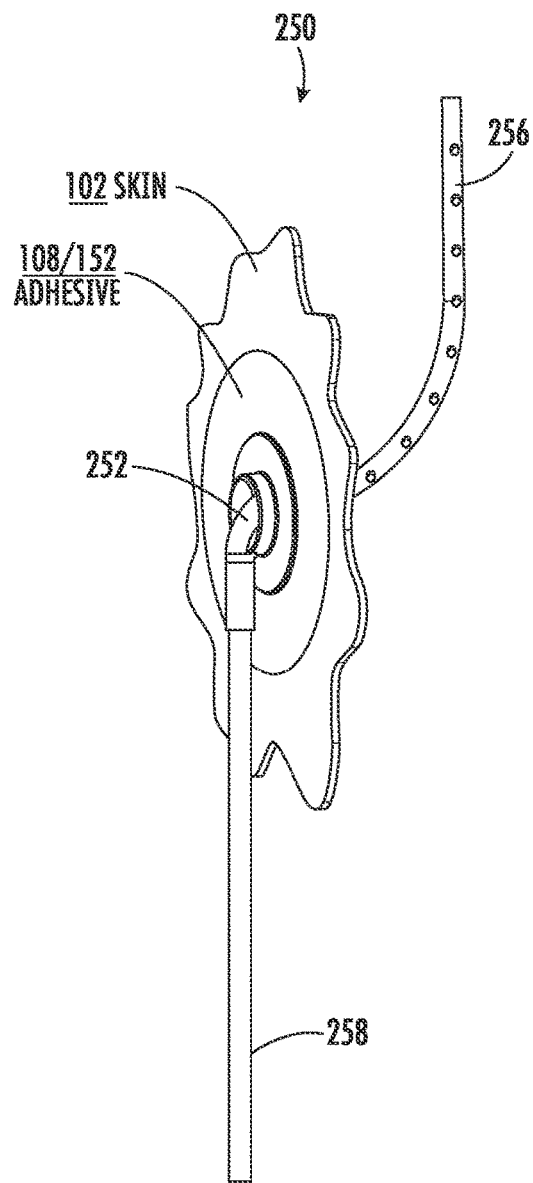 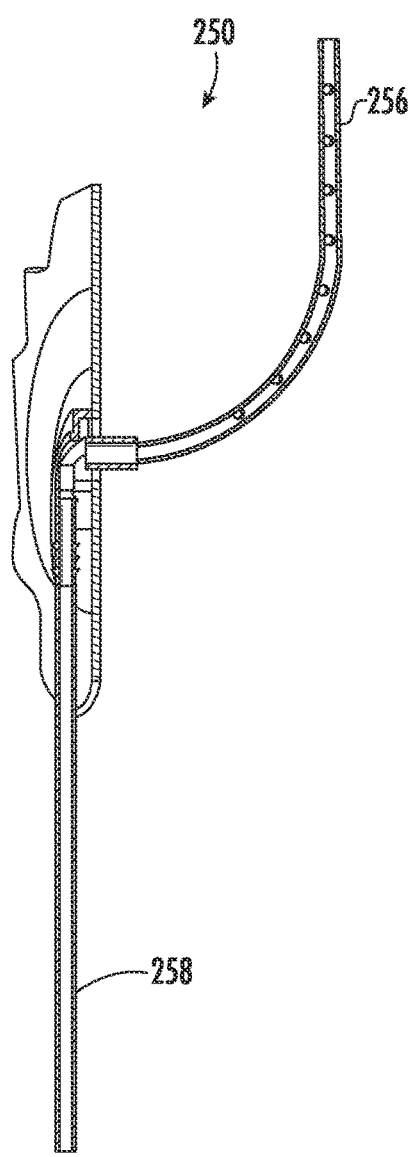
FIG. 14A
FIG. 14B

OUTWARD FLOW: FREE

INWARD FLOW: CHECKED

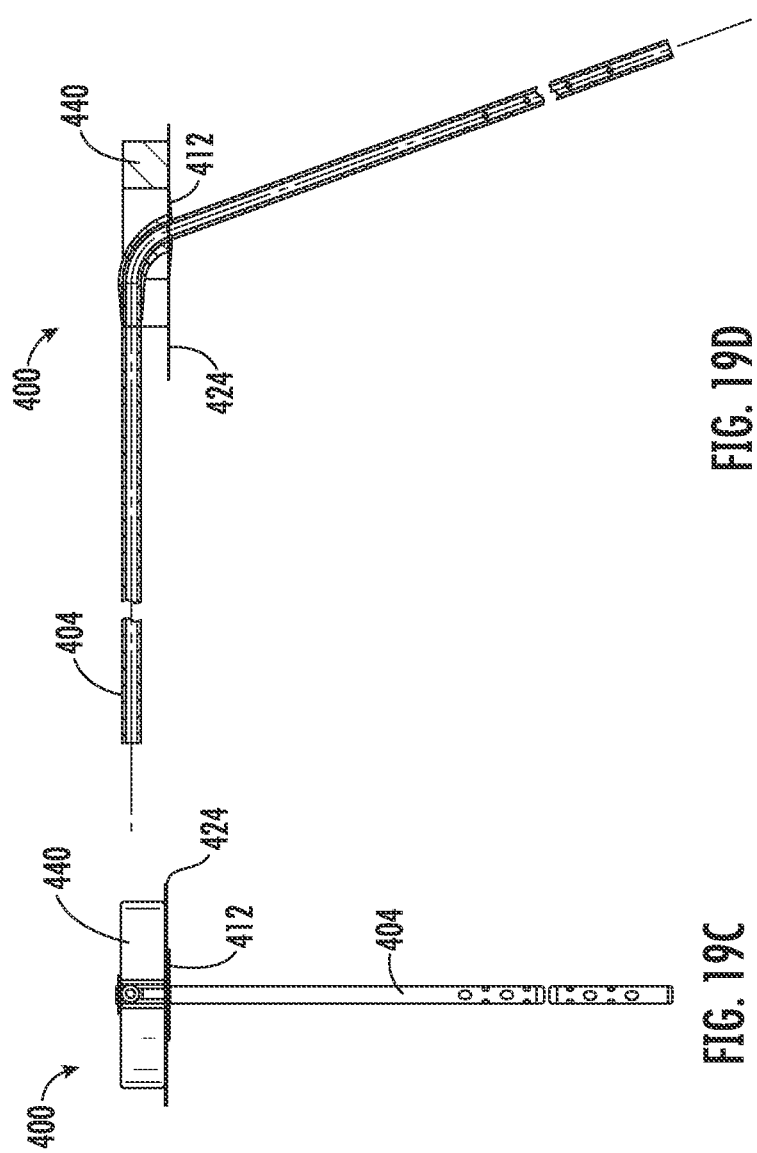

CATHETER ANCHOR APPARATUS AND METHODS

RELATED APPLICATIONS

This application is a 35 U.S.C. § 371 national stage application of International Application No. PCT/US2021/054699, entitled "Improved Catheter Anchor Apparatus and Methods," filed on Oct. 13, 2021, which claims the benefit of U.S. Provisional Application Ser. No. 63/091,847, filed on Oct. 14, 2020. The entire contents of the above-referenced applications are incorporated herein by this reference.

TECHNICAL FIELD

Embodiments of the present invention generally relate to the field of medical devices. More particularly, various embodiments relate to improved devices and methods for anchoring a catheter or the like to a human body.

BACKGROUND

Following surgery, it is known to install a drain percutaneously to allow excess fluids at the surgical site to drain from the body during post-operative healing. The drain typically comprises a length of tubing that extends from the interior of a patient's body through an opening in the patient's skin to a collection bulb disposed at a distal end of the tubing. The drain tubing is then anchored to the skin at the insertion site in order to keep the tubing from sliding out of the body.

Various tubing anchors, sometimes also referred to as fixation devices or stabilization devices, are known for this purpose. However, the current standard of care for anchoring a surgical drain is the "Roman garter" technique. With reference to FIG. 1, a length of tubing 10 is shown extending from a drain opening 12 in a patient's skin 14. The length of tubing 10 is wrapped with a suture 16 and stitched at 18 to the skin 14. The patient lives with the tubing 10 protruding through his or her skin for about one to two weeks after the surgery. When the flow rate of the fluid drops below a minimum threshold (e.g., 30 ml/24 hours) the drain tube is removed by cutting the suture 16 and then pulling the tubing 10 out of the body.

The foregoing discussion is intended only to illustrate various aspects of the related art in the field of the invention at the time, and should not be taken as a disavowal of claim scope.

SUMMARY

In accordance with one embodiment, the present invention provides an anchor assembly for securing at least one catheter to a human body. The anchor assembly comprises an anchor formed of an elastomeric material, the anchor comprising an anchor body and a flange depending from the anchor body. The flange defines a first side adjacent the anchor body and a second side opposite the first side. An adhesive dressing is disposed over the flange first side. The adhesive dressing comprises a first portion and a second portion. The first portion at least partially covers the first side of the flange, and the second portion is positioned laterally outward of the flange relative to the anchor body.

In various embodiments, the flange is annular in shape and defines a first diameter, and the adhesive dressing is annular and shape and defines a second diameter greater than the first diameter. In some embodiments, the elastomeric material comprises silicone. In some embodiments, a collar surrounds the anchor body and is disposed between the adhesive dressing and the flange first side. In some embodiments, the anchor further comprises a fitting disposed at least partially within the anchor body, wherein the fitting defines an internal bore and at least one connection member, and the at least one catheter is releasably coupled with the connection member and in fluid communication with the internal bore. In some embodiments, the fitting comprises a check valve. In some embodiments, the fitting comprises a first connection member and a second connection member, a first catheter is coupled with the first connection member, a second catheter is coupled with the second connection member, and the first catheter is in fluid communication with the second catheter. In various embodiments, a single catheter extends through a bore defined in the anchor body and coupling. In some embodiments, an application layer is releasably coupled with the adhesive dressing. In some embodiments, a compression layer is coupled with the application layer.

In accordance with another embodiment, the present invention provides an anchor assembly for securing a catheter. An anchor assembly includes an anchor comprising an anchor body and a flange coupled with the anchor body. The flange has a top side and a bottom side opposite the top side, the bottom side configured to engage a human body. The anchor body defines at least one bore configured to receive a catheter therein. An adhesive dressing is disposed on the top side of the flange. The adhesive dressing includes a first portion and a second portion. The first portion at least partially covers the first side of the flange, and the second portion extends radially outward of the flange relative to the anchor body. In various embodiments, the anchor assembly also comprises a compression layer releasably coupled with the adhesive dressing. In some embodiments, a collar is disposed between the adhesive dressing and the flange top side.

In accordance with a further embodiment, the present invention provides an anchor assembly for securing a catheter to a human body. The anchor assembly comprises an anchor, the anchor comprising an anchor body and a flange coupled with the anchor body. The flange has a top side and a bottom side opposite the top side. The bottom side is configured to engage the human body. The anchor assembly further comprises a collar disposed around the anchor body, the collar having a bottom side engaging the flange top side and an opposite top side. The anchor assembly also comprises a dressing, the dressing having a bottom side coupled with the collar top side and the flange top side. The dressing has a top side opposite the dressing bottom side. The anchor assembly also comprises an application layer releasably coupled with the dressing top side and a compression layer coupled with the application layer.

In various embodiments, the application layer comprises polyethylene terephthalate. In some embodiments, the compression layer is formed from a closed cell foam material. In some embodiments, the collar comprises a polycarbonate material. In various embodiments, the anchor assembly further comprises a removable liner layer coupled with the dressing bottom side.

In accordance with yet another embodiment, a method of securing a catheter to a human body is provided. The method comprises providing an anchor assembly. The anchor assembly comprises an anchor comprising an anchor body, a flange depending from the anchor body, and an internal bore extending between a distal end of the anchor body and an opening defined in the flange. At least one catheter is coupled with the anchor and in fluid communication with the internal bore. An adhesive layer is coupled with the flange and extends radially outward thereof. The adhesive layer has a first side adjacent the flange and a second side opposite the first side. A first liner layer is releasably attached with the adhesive layer first side. A compression layer is releasably coupled with the adhesive layer second side. The method also comprises inserting at least a portion of the at least one catheter in a passage of the human body. Also, the method includes removing the first liner layer from the anchor assembly to expose an adhesive on the first side of the adhesive layer. The method further includes adhering the adhesive layer to the human body, applying a compressive force to the compression layer, and removing the compression layer from the adhesive layer. In various embodiments, the anchor assembly further comprises an application layer disposed between the compression layer and the adhesive layer second side.

BRIEF DESCRIPTION OF THE DRAWINGS

Figure 1:
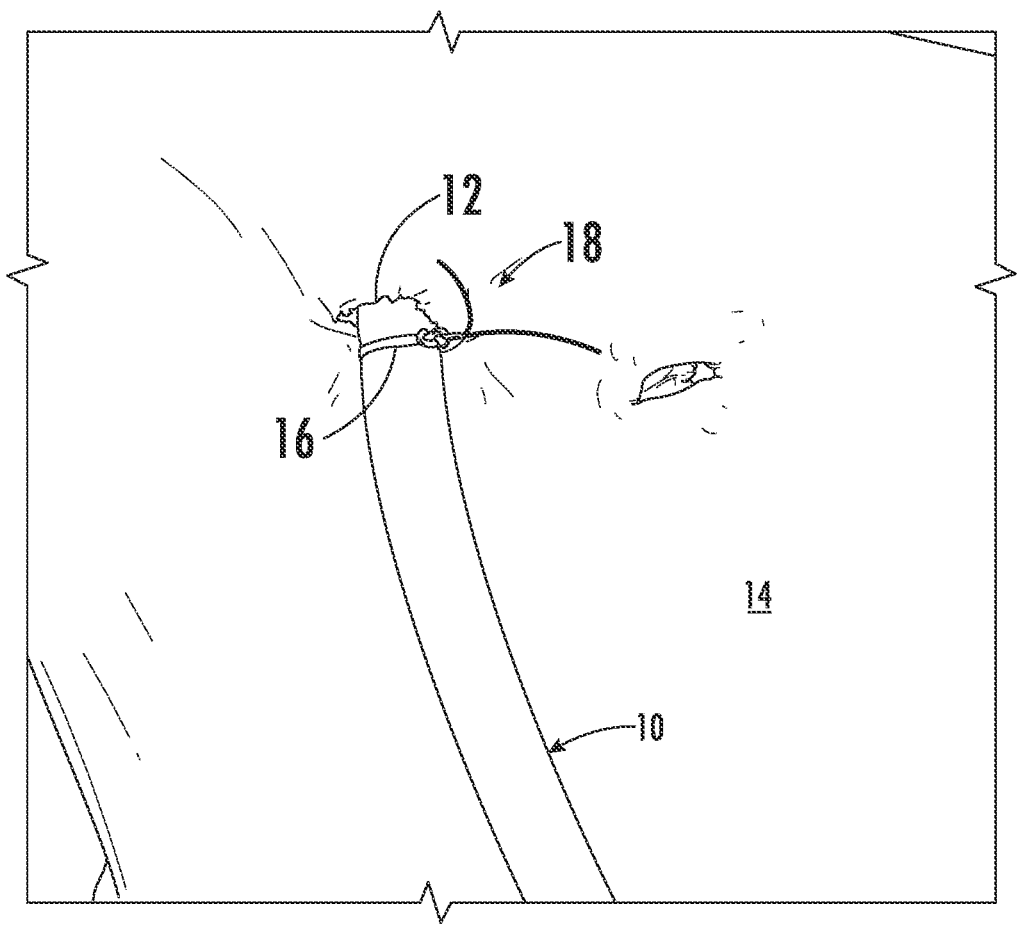
Figure 2:
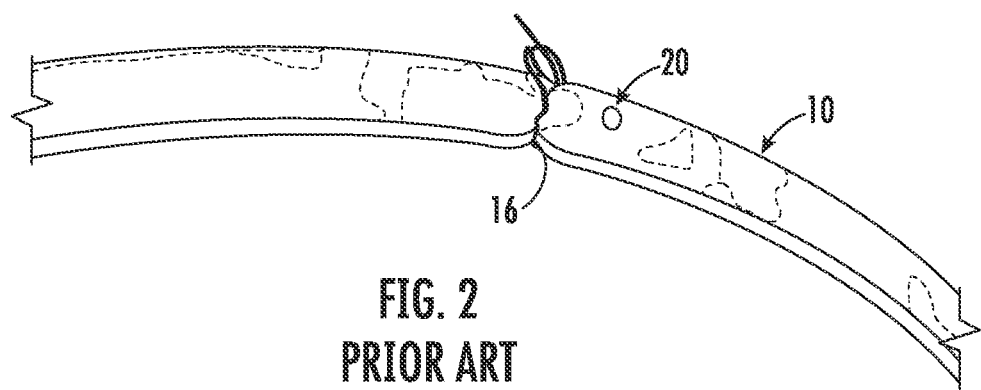
Figure 3:
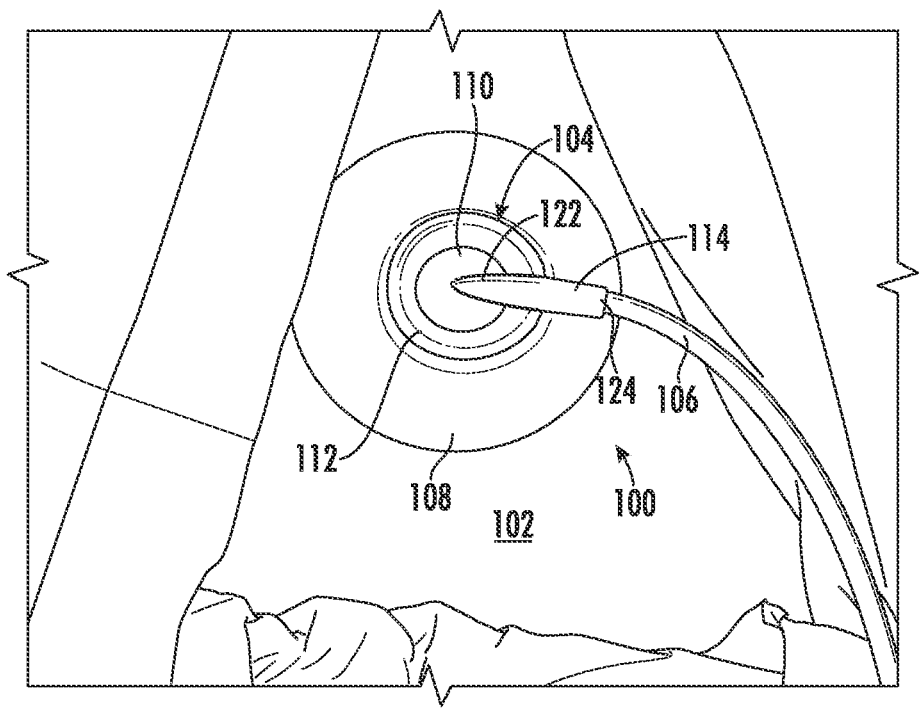
Figure 4:
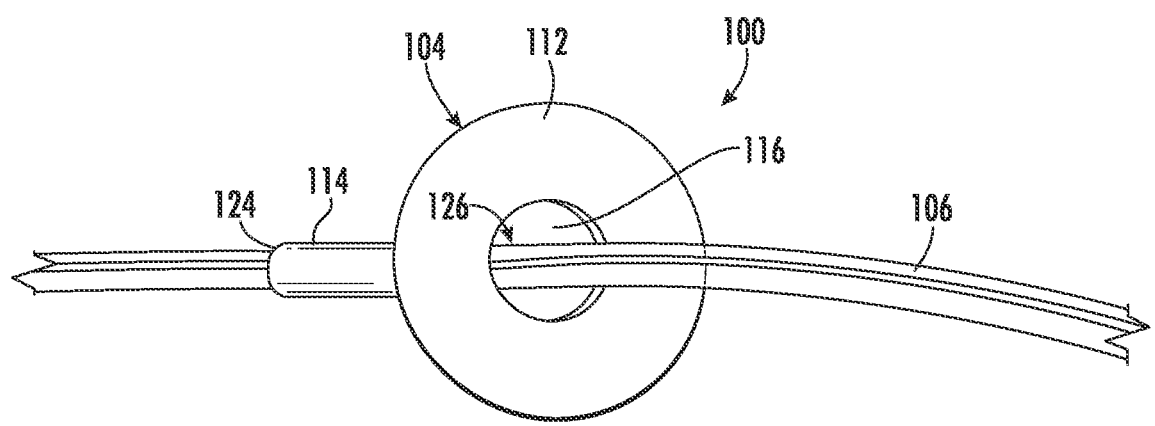
Figure 5:
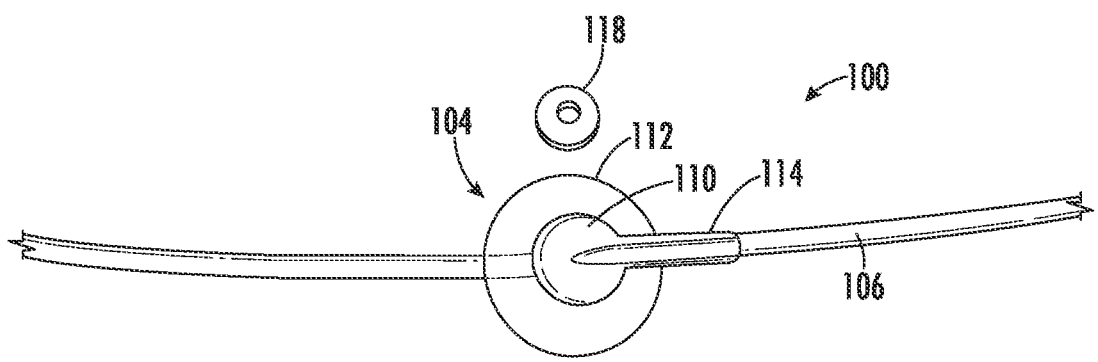
Figure 6:
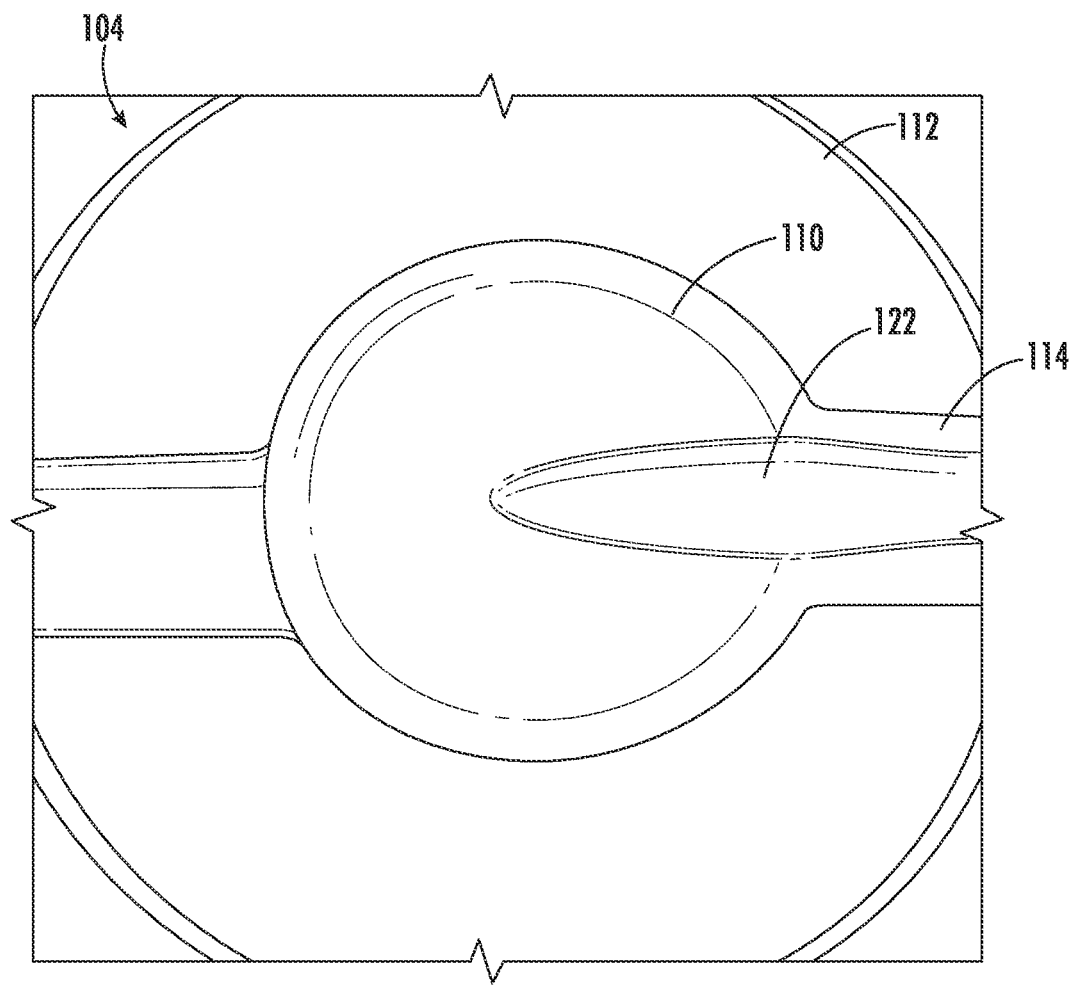
Figure 7:
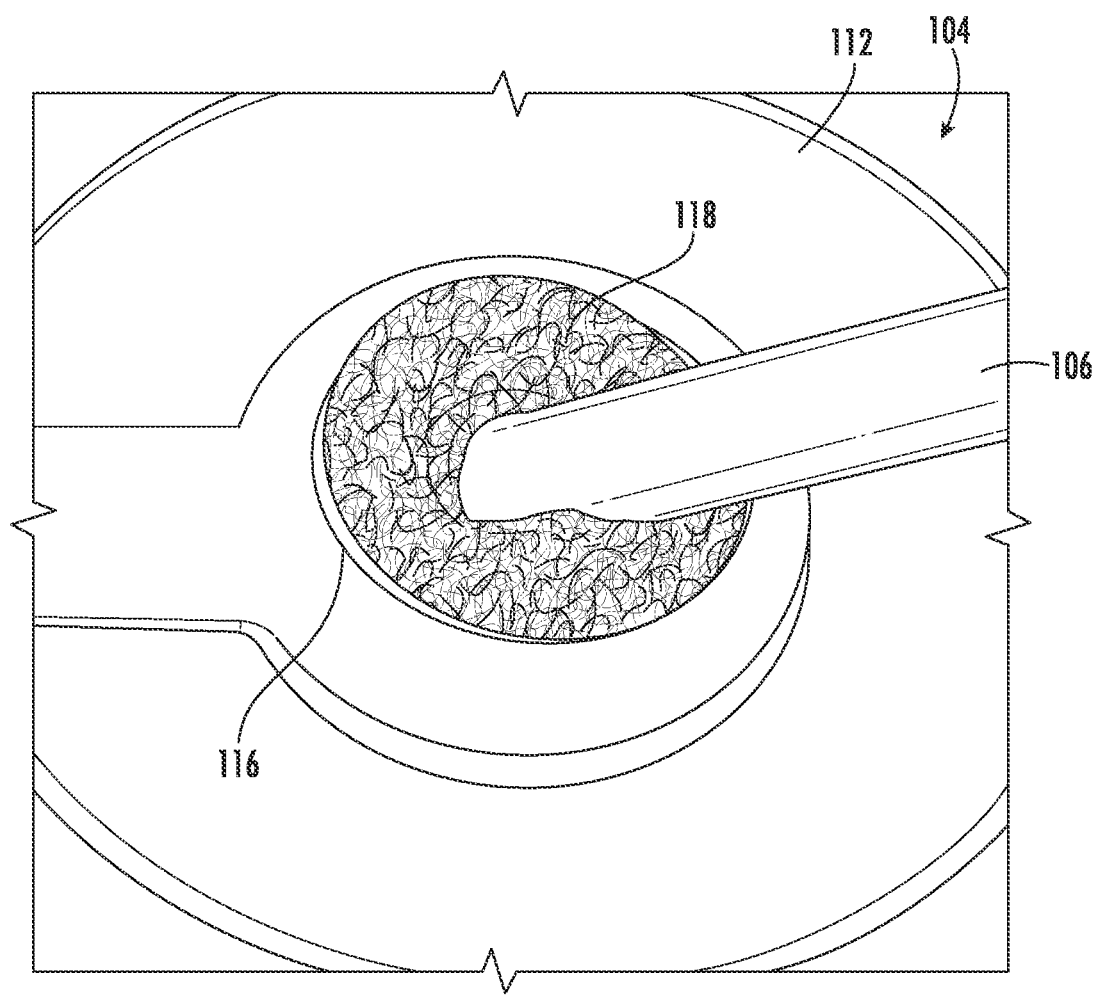
Figure 8:
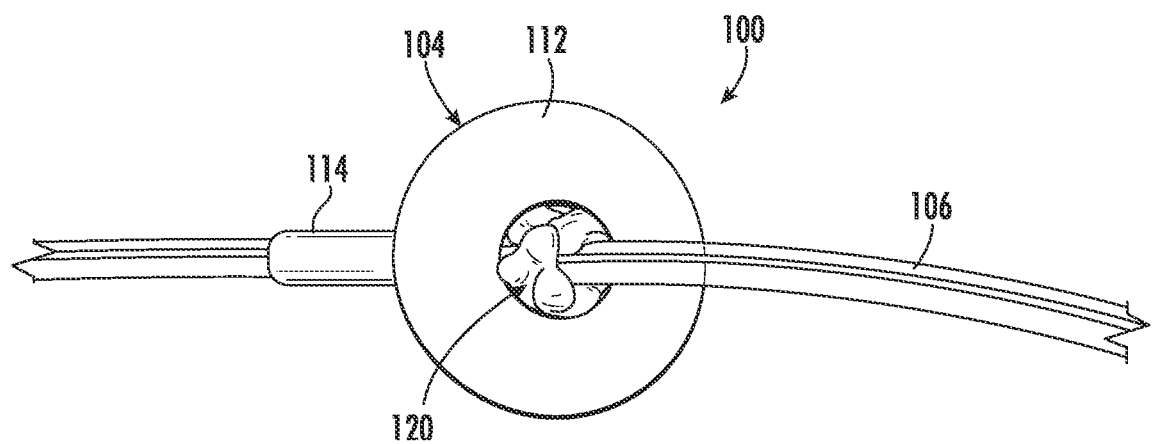
Figure 9:
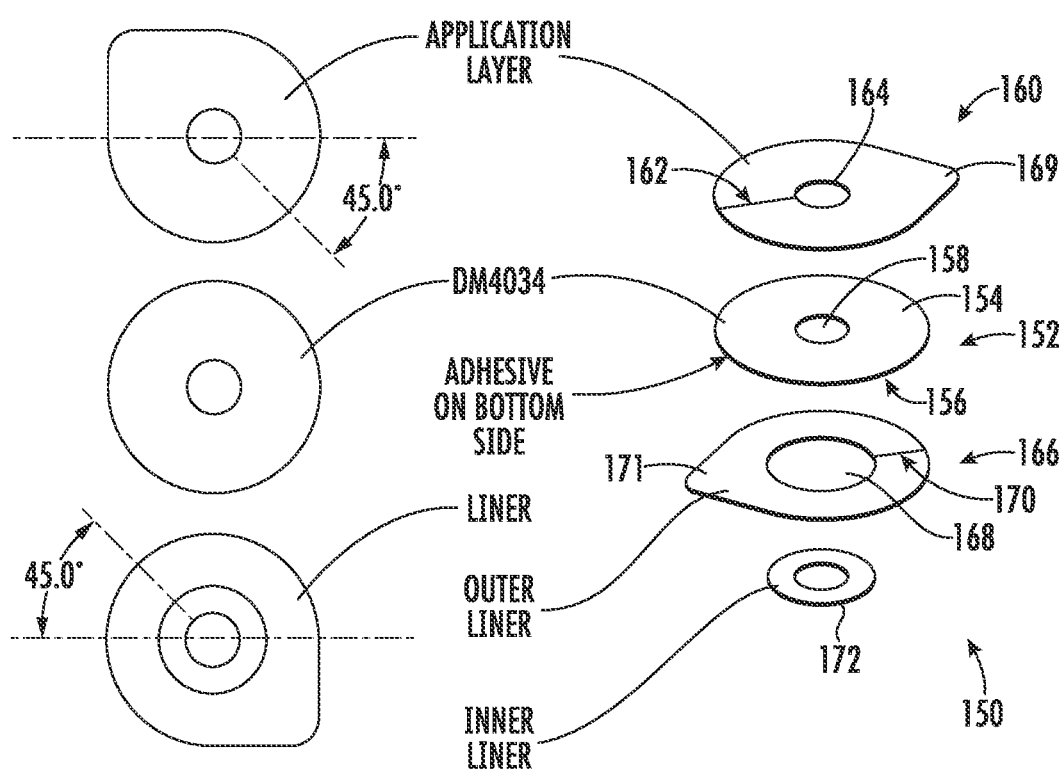
Figure 10A:
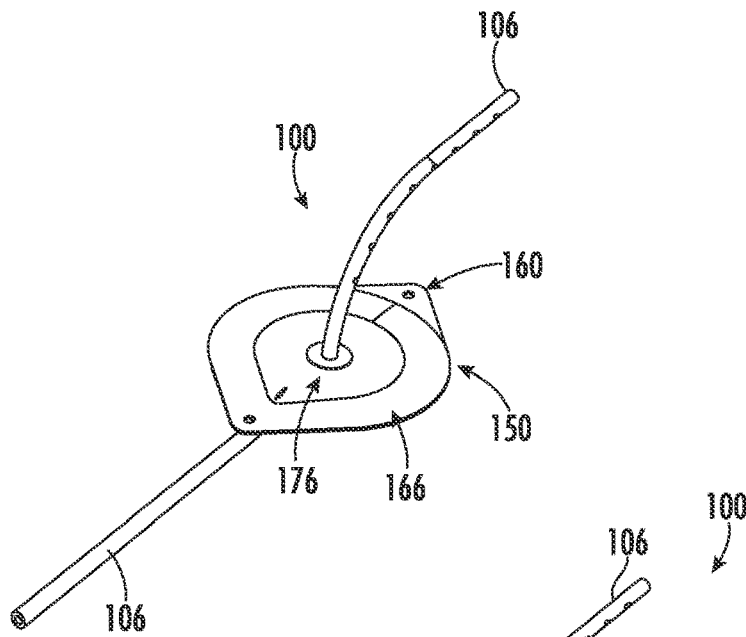
Figure 10B:
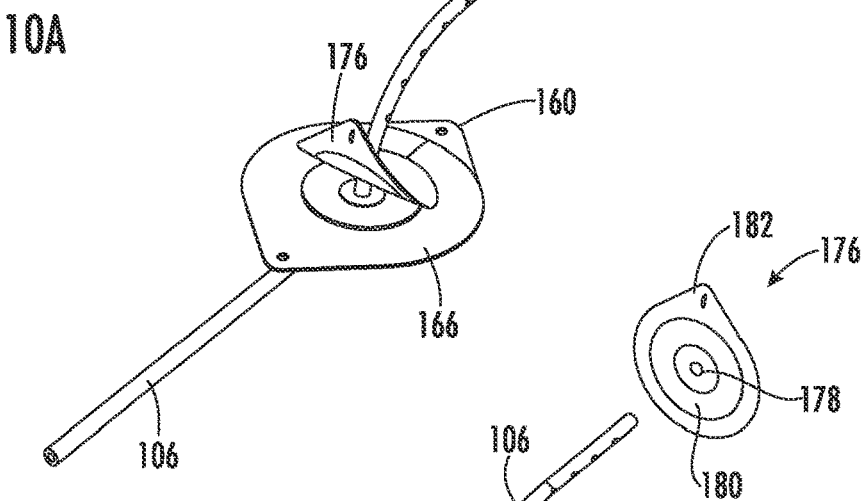
Figure 10C:
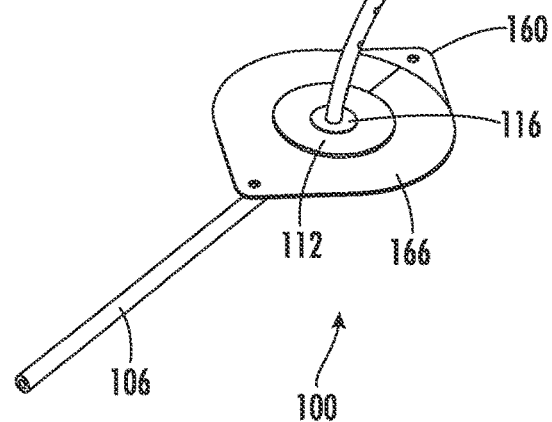
Figure 11A:
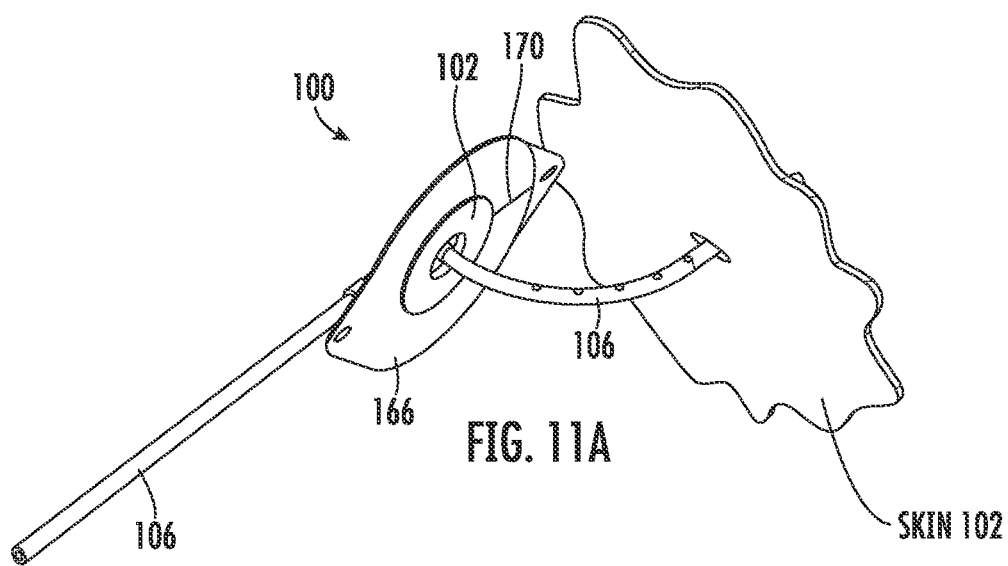
Figure 11B:
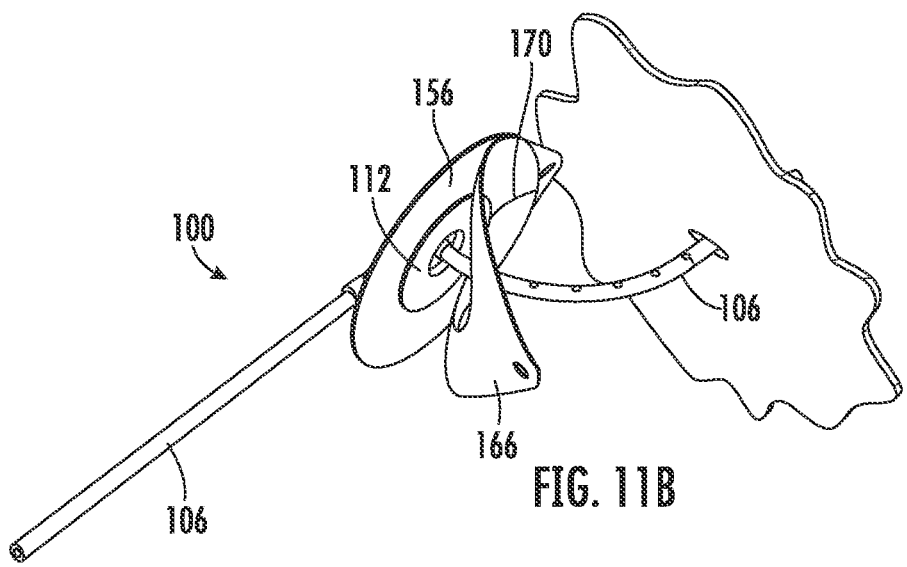
Figure 11C:
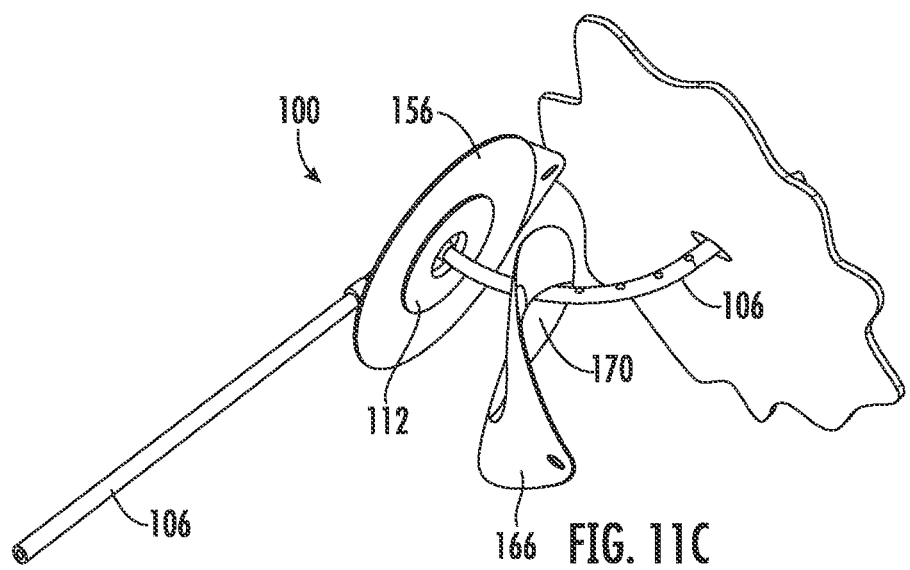
Figure 12A:
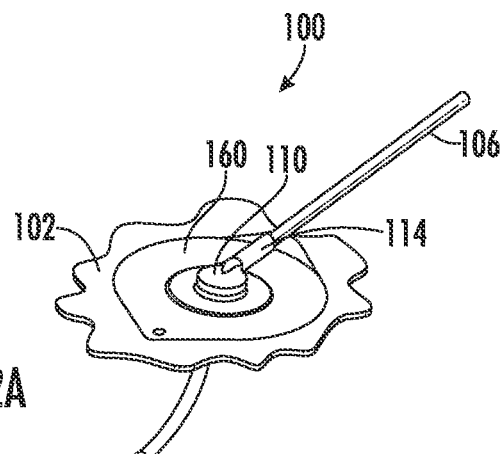
Figure 12B:
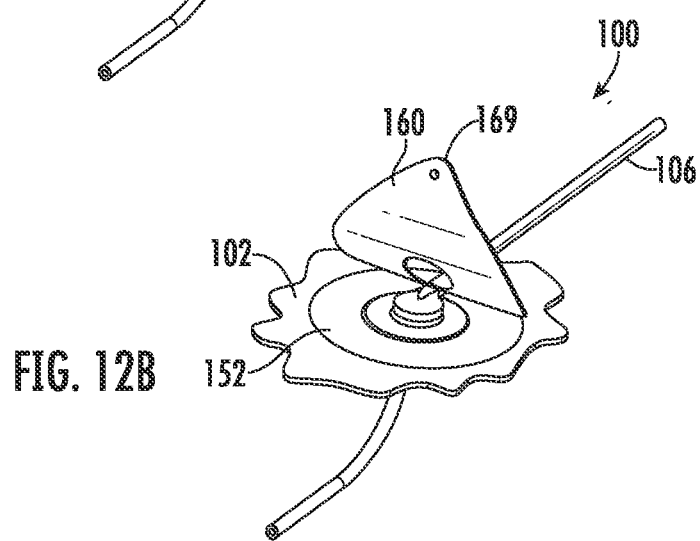
Figure 12C:
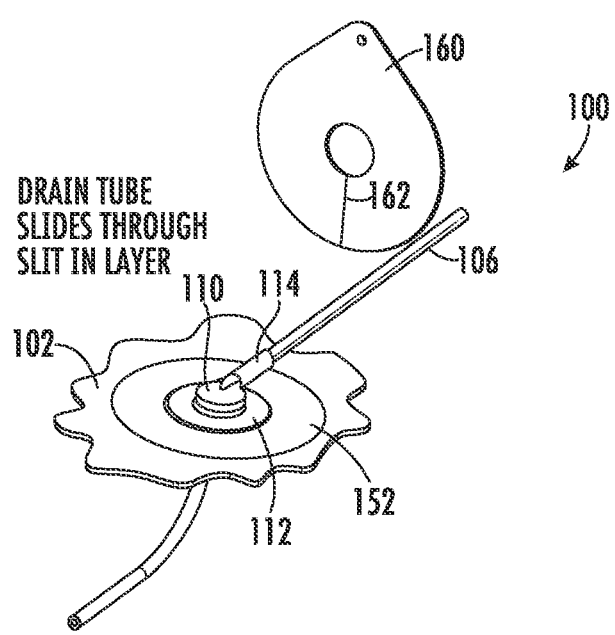
Figures 13A, 13B:
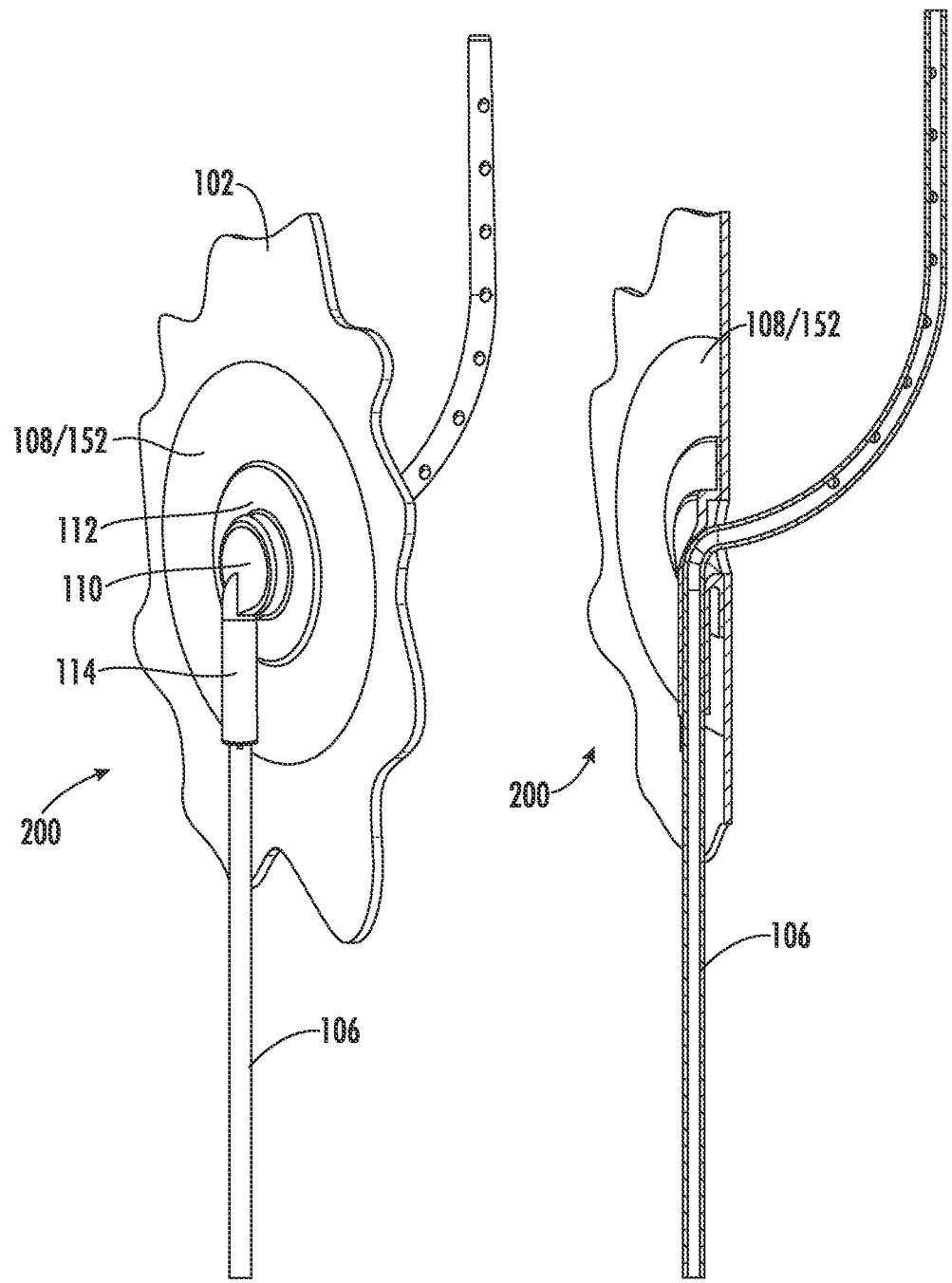
Figure 15A:
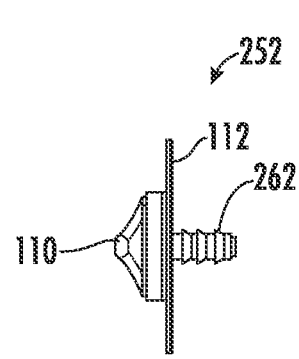
Figure 15B:
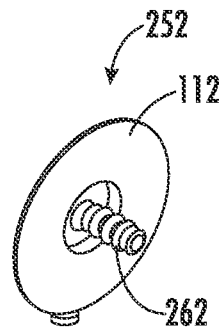
Figure 15C:
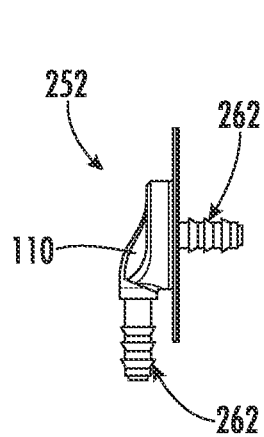
Figure 15D:
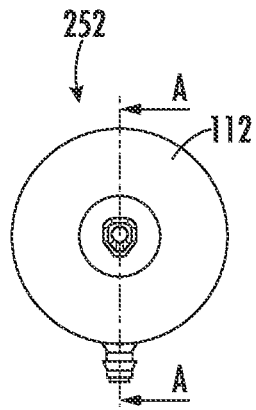
Figure 15E:
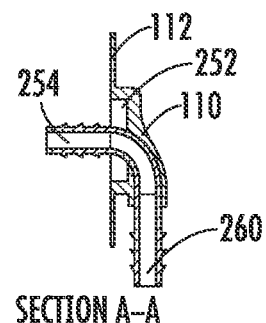
Figure 16A:
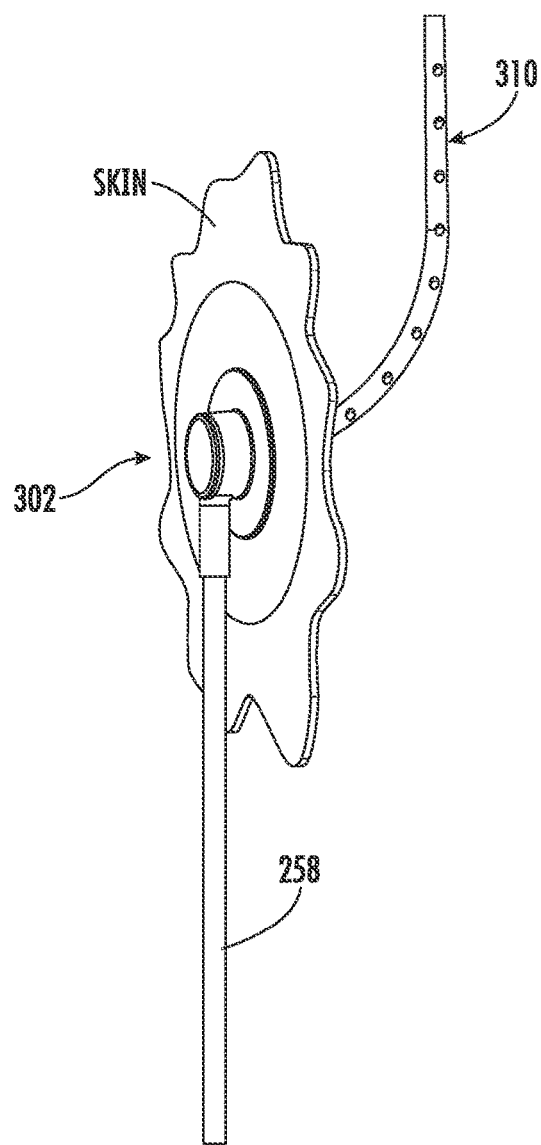
Figure 16B:
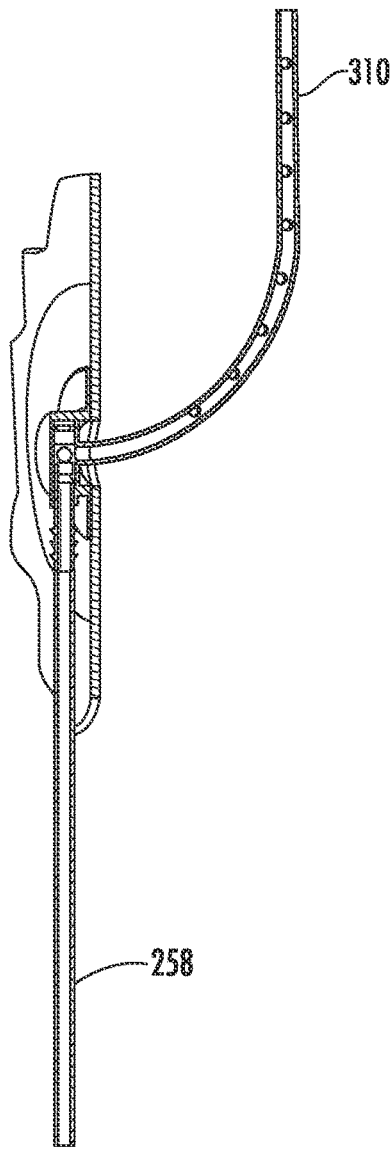
Figure 17A:
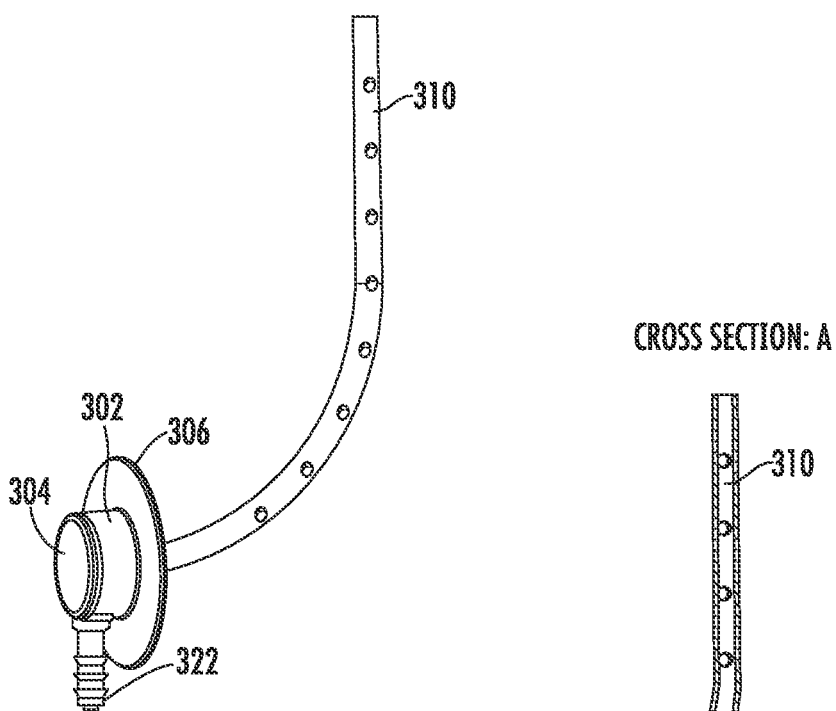
Figure 17B:
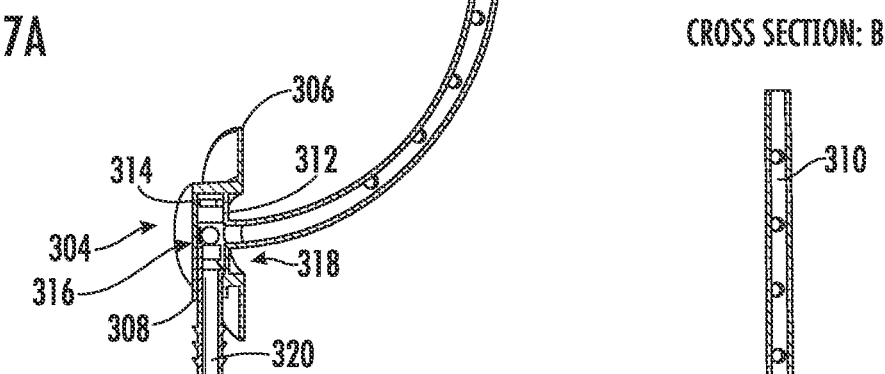
Figure 17C:
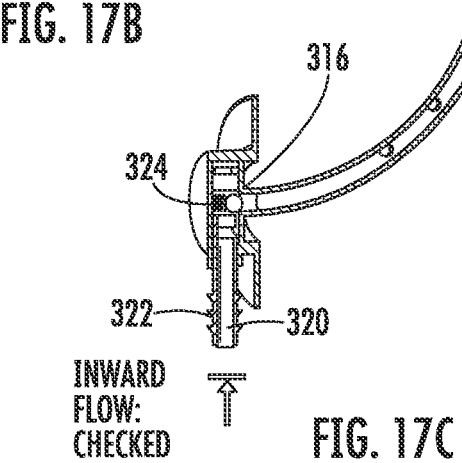
Figure 18:
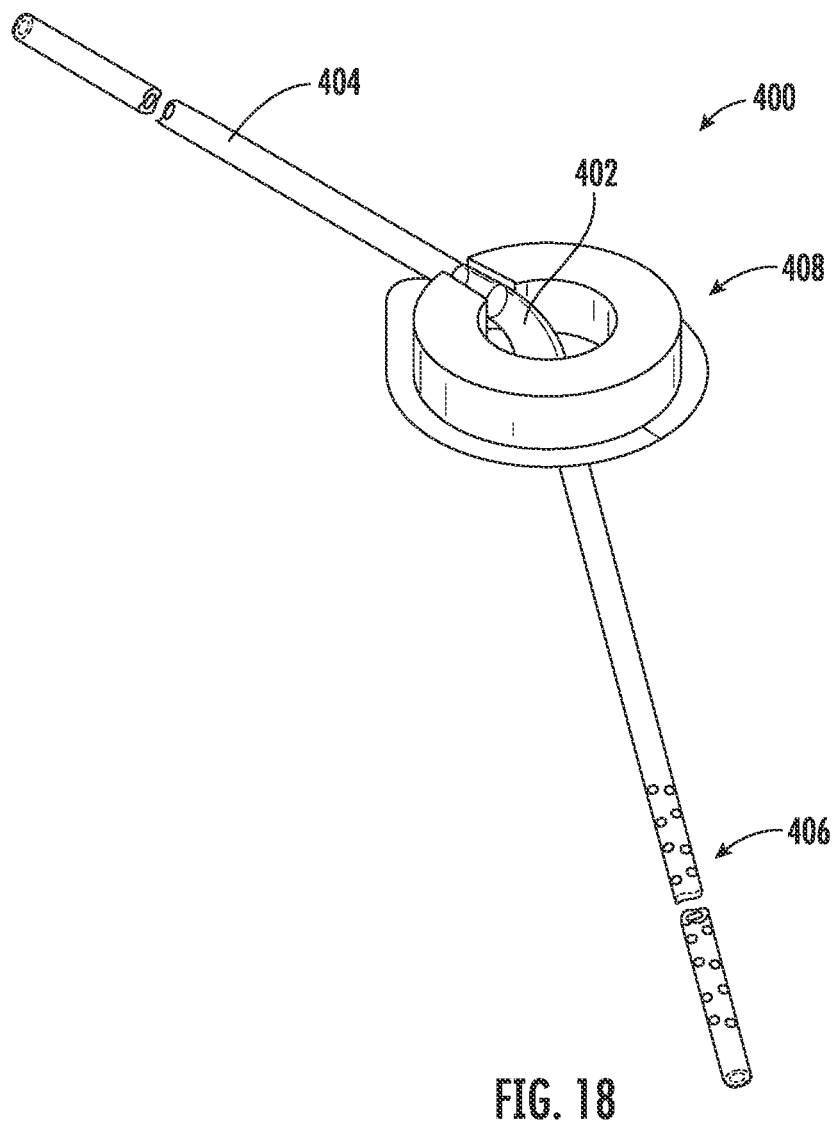
Figure 19A:
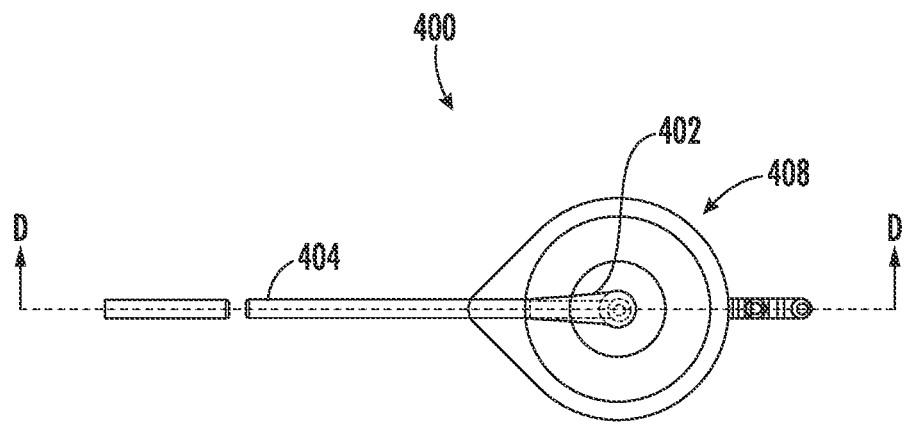
Figure 19B:
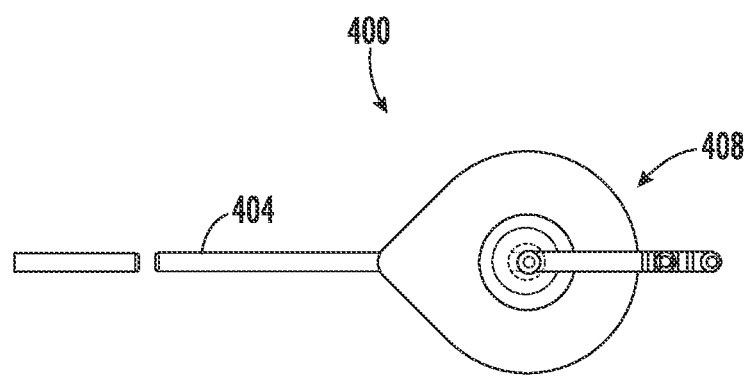
Figure 20:
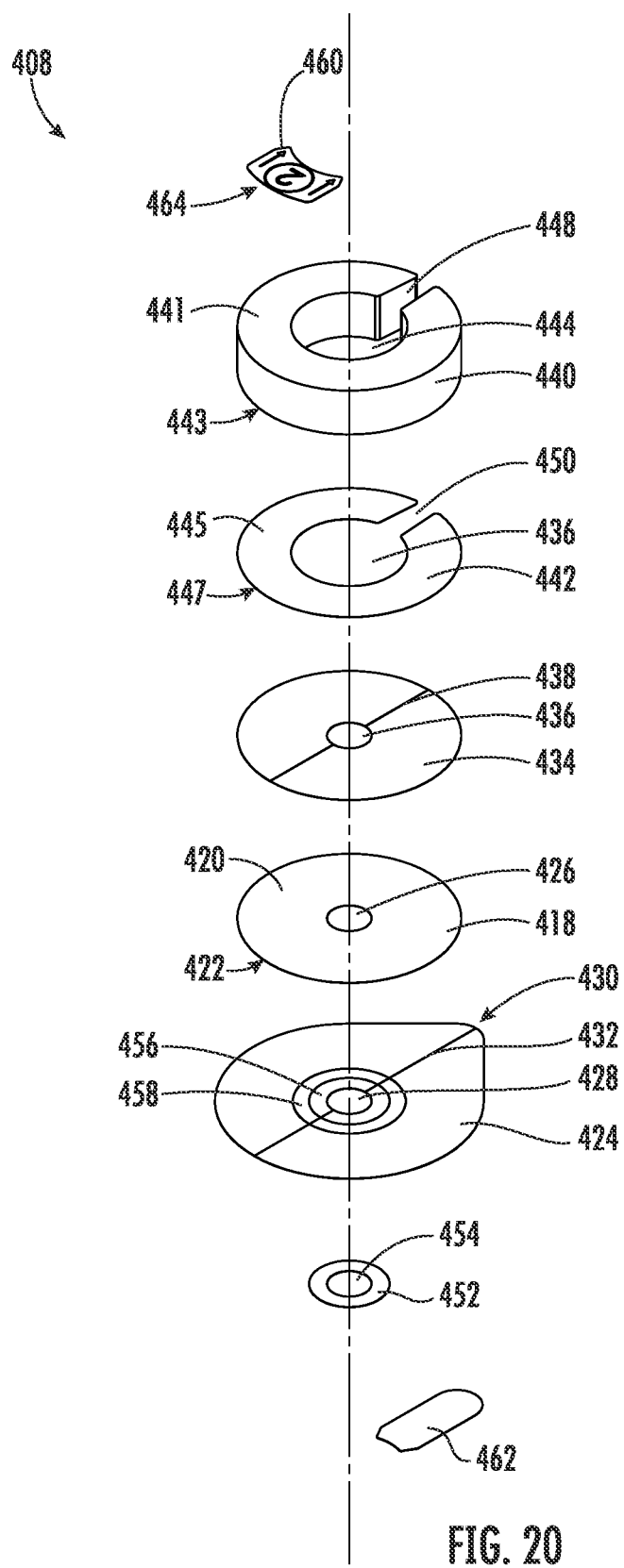
Figure 21A:
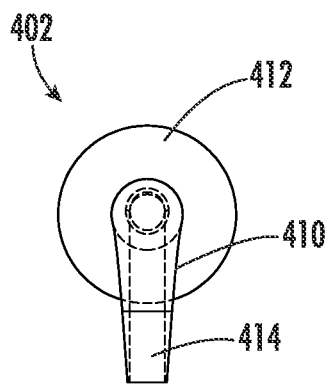
Figure 21D:
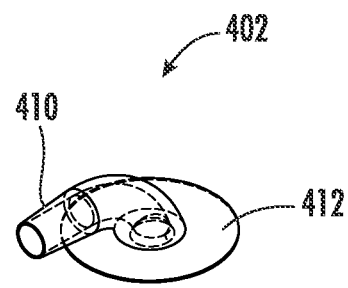
Figure 21B:
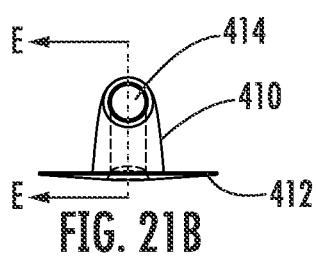
Figure 21E:
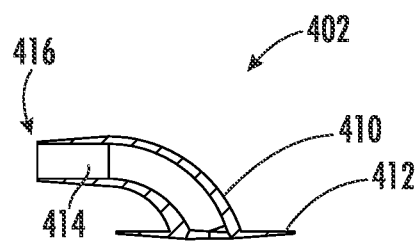
Figure 21C:
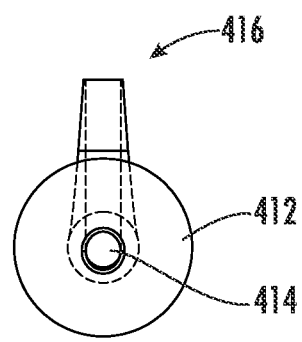
Figures 22A, 22B:
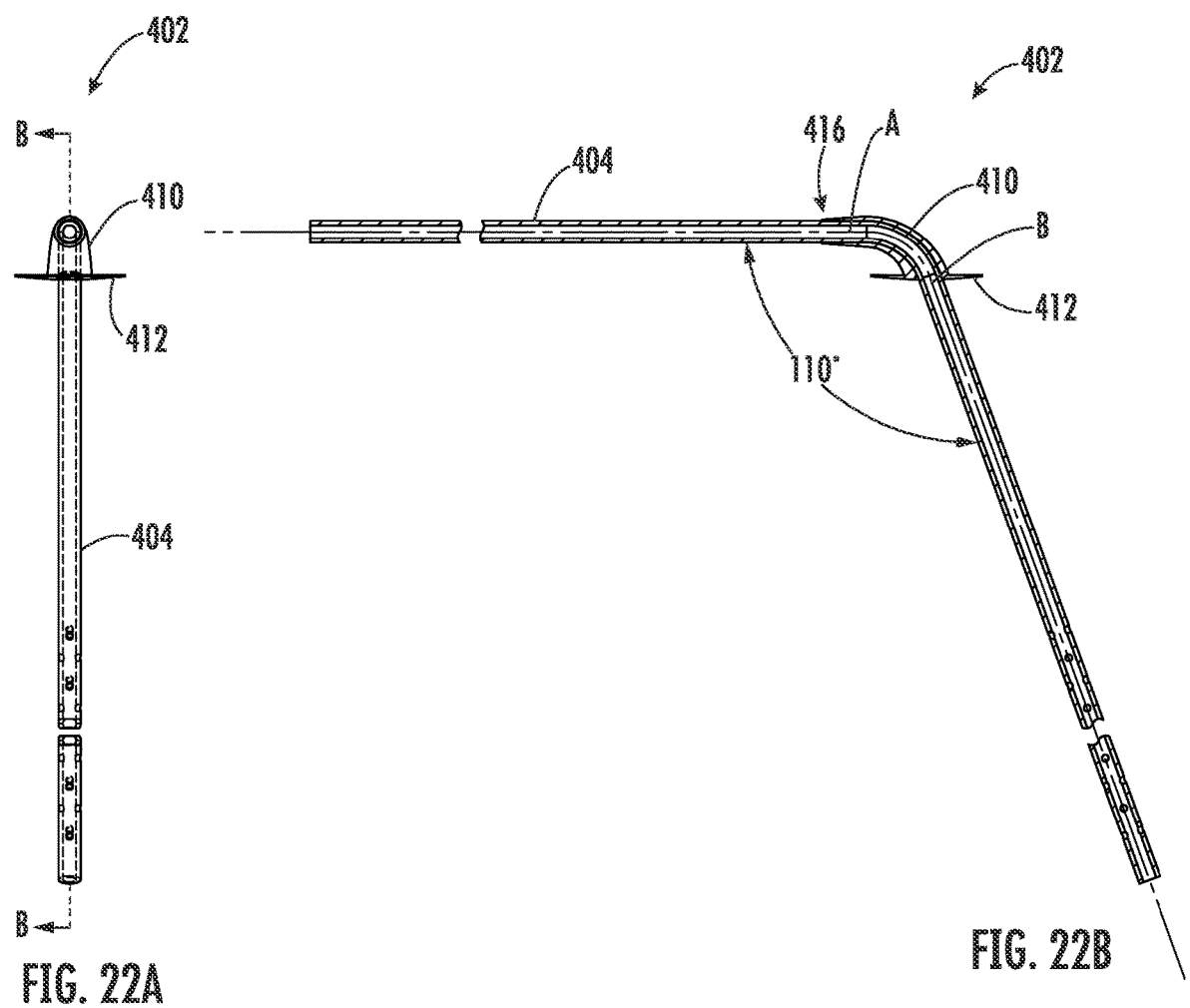

Having thus described some example embodiments in general terms, reference will now be made to the accompanying drawings, which are not necessarily drawn to scale, and wherein:

FIG. 1 is a perspective view of a prior art surgical drain secured to a human body using the Roman garter technique;

FIG. 2 is a perspective view of a prior art catheter used in a surgical drain following removal of the catheter from the drain with a suture still tied around the catheter:

FIG. 3 is a perspective view of an anchor assembly affixed to the skin of a patient and securing a drainage catheter with respect to a surgical site in accordance with an embodiment of the present invention;

FIG. 4 is a perspective view of the skin-facing side of an anchor assembly in accordance with an embodiment of the present invention, wherein the adhesive dressing is not shown;

FIG. 5 is a perspective view of the exterior-facing side of the anchor assembly of FIG. 4 shown with a sponge impregnated with a topical therapeutic:

FIG. 6 is an enlarged partial plan view of the exterior-facing side of the anchor assembly of FIG. 4 wherein the impregnated sponge is disposed within a cavity of the anchor:

FIG. 7 is an enlarged perspective view of the skin-facing side of the anchor assembly of FIG. 6;

FIG. 8 is a perspective view of the skin-facing side of the anchor assembly of FIG. 4 wherein an ointment topical therapeutic is disposed within a cavity of the anchor;

FIG. 9 is an exploded view of an adhesive dressing for an anchor assembly in accordance with an embodiment of the present invention:

FIGS. 10A-10C illustrate removal of a seal for a cavity of the anchor in accordance with an embodiment of the present invention:

FIGS. 11A-11C illustrate insertion of a catheter into a surgical site and removal of an liner of an adhesive dressing in accordance with an embodiment of the present invention:

FIGS. 12A-12C illustrate adhering an anchor assembly to the skin and removal of an application layer of an adhesive dressing in accordance with an embodiment of the present invention;

FIG. 13A is a perspective view of an anchor assembly in accordance with another embodiment of the present invention:

FIG. 13B is a perspective cross-sectional view of the anchor assembly of FIG. 13A taken along a line extending parallel with the longitudinal axis of the catheter;

FIG. 14A is a perspective view of an anchor assembly in accordance with another embodiment of the present invention:

FIG. 14B is a perspective cross-sectional view of the anchor assembly of FIG. 14A taken along a line extending parallel with the longitudinal axis of the catheter:

FIGS. 15A-15E are various views of an anchor fitting in accordance with an embodiment of the present invention:

FIG. 16A is a perspective view of an anchor assembly in accordance with another embodiment of the present invention:

FIG. 16B is a perspective cross-sectional view of the anchor assembly of FIG. 16A taken along a line extending parallel with the longitudinal axis of the catheter;

FIG. 17A is a perspective view of an anchor assembly having an integrated internal tube in accordance with another embodiment of the present invention:

FIGS. 17B-17C are perspective cross-sectional views of the anchor assembly of FIG. 17A illustrating operation of a check valve disposed within the anchor;

FIG. 18 is a perspective view of an anchor assembly in accordance with another embodiment of the present invention:

FIGS. 19A-B are respective top and bottom plan views of the anchor assembly of FIG. 18:

FIGS. 19C and E are respective front and back elevation views of the anchor assembly of FIG. 18:

FIG. 19D is a cross-sectional view taken along the line D-D in FIG. 19A:

FIG. 20 is an exploded view of an adhesive subassembly for use with an anchor in accordance with an embodiment of the present invention:

FIGS. 21A-D are respective top plan, front elevation, bottom plan, and perspective views of an anchor in accordance with an embodiment of the present invention:

FIG. 21E is a cross-sectional view taken along the line E-E in FIG. 21B;

FIG. 22A is a front elevation view of an anchor coupled with a catheter in accordance with an embodiment of the present invention; and FIG. 22B is a cross-sectional view taken along the line B-B in FIG. 22A.

Repeat use of reference characters in the present specification and drawings is intended to represent same or analogous features or elements of embodiments of the present invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Further, either of the terms "or" and "one of A and B," as used in this disclosure and the appended claims is intended to mean an inclusive "or" rather than an exclusive "or." That is, unless specified otherwise, or clear from the context, either of the phrases "X employs A or B" and "X employs one of A and B" is intended to mean any of the natural inclusive permutations. That is, either phrase is satisfied by any of the following instances: X employs A: X employs B: or X employs both A and B, regardless whether the phrases "at least one of A or B" or "at least one of A and B" are otherwise utilized in the specification or claims. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

There are a number of problems with presently-available methods and apparatuses for anchoring a surgical drain. For example, one such problem is patient discomfort. In that regard, where the Roman garter technique is used, about 18 inches of tube and a collection bulb with up to 100 ml of fluid can be anchored by one or two stitches. Patients are advised to clip the collection bulb to their clothing so it does not hang from the tube anchor, but invariably at times the bulb is not secured and the suture supports the full weight of the drain system. Because the drain tube incision point is an open wound for the duration of the drain period, the skin around becomes inflamed and tender. Adding a stitch so close to the incision only exacerbates the discomfort to the point that any movement of the tube is painful. This discomfort also can contribute to lack of sleep.

Further, where the Roman garter technique is used, there is often a risk of tube migration or accidental removal. Even when properly knotted, a suture anchor could loosen and allow for tube slippage. A single suture through the skin is also not a very robust connection. In this regard, patients regularly drop the drain bulb full of fluid, and when dropped unrestrained the full length of the tube, the impact on the tube can yank the tube through loose sutures or the stitch through the skin. Sometimes this will pull the drain tube out of the body. This can require a painful and costly emergency visit to the surgeon to reinsert the drain tube.

Another consideration is the time it takes to perform the Roman garter technique. Surgeons take anywhere from 20 seconds to 5 minutes to properly tie off the drain tube and stitch it to the skin in current systems. If, for example, the average cost of a staffed surgical suite is $1700/hour, that is equivalent to $0.47/second. Therefore, the cost of the time to perform the technique can be estimated to cost between $9.44 and $141.67. In surgery, every second counts, and the inventor has recognized that a faster anchoring solution may reduce a patient's time on the table and may also save money.

Finally, known suture-based methods often lead to the development of scar tissue from a long term open wound. In particular, the drain tube insertion point is an open wound and is subject to infecting bacteria which can increase scarring. Many surgeons leave the insertion site open to the air because of the difficulty of properly sealing the site. This allows exposure to bacteria and the skin around the incision begins to dry out and scab.

Attempts have been made to improve on suture-based tube anchors, including via a variety of different commercially available devices for securing a catheter in place. While some of these devices do a good job of moving the attachment to the skin away from the incision point, so when the tube is pulled the stress is not transferred to the wound, most such devices use hard plastic components and have sharp corners. Again, this increases user discomfort when the devices are pressed or scraped against other parts of the body. These devices also do not address the other problems mentioned above.

Another problem with current systems and methods lies in reduced flow from restriction and clotting. More particularly, and with reference to FIG. 2, in current systems, in order for the suture 16 to grip the tubing 10 so that the tubing 10 does not slide out of the body, the suture 16 loops need to compress the tube. In part because the suture 16 is narrow in width, the stress of compressing the tubing 10 deforms the tubing 10 where the suture 16 is gripping it, resulting in a location at which the inside diameter of the tubing 10 is reduced. This reduced inside diameter causes a point of constriction, so solid lipid masses and blood clots 20 cannot pass. This restriction of solids has the potential to fully block the flow of drain fluid. As shown in FIG. 2, after the tubing 10 is removed from the drain, the suture 16 is still around tube holding the blood clots 20 from draining out. Again, although attempts have been made to improve upon suture-based attachment, most presently-available devices clamp the tubing in some way, such as via a narrow band. This again deforms the tubing, constricting the flow of fluid through the tubing.

In contrast, embodiments of the present invention comprise apparatus and methods for anchoring a catheter to a human body that overcome the above-mentioned and other problems. For example, some embodiments provide an anchor assembly comprising an elastomeric anchor that flexes to conform to a patient's body's contours, that does not have any hard surfaces that are uncomfortable to the wearer (such as when the wearer rolls over on it or bumps against it), and that absorbs the forces or shock of accidental tugs on the catheter. Further, in some embodiments, the anchor defines a cavity configured to receive, hold, and/or administer a topical therapeutic. Further, in some embodiments, the anchor comprises a flange designed to move the retention stress of the attachment to the skin radially away from the incision or opening through which the catheter passes to reduce pain and discomfort. Additionally, in some embodiments, the anchor comprises one or more couplings for a catheter that securely retains the catheter(s) with respect to the anchor without cinching a cable tie, suture, band, or the like around the catheter to facilitate attachment, thus preventing that the catheter(s) are not crimped and do not suffer a reduction in inside diameter. Therefore, various embodiments prevent flow restrictions or catching of solids. These and other inventive aspects of the present disclosure are discussed in greater detail below.

Certain embodiments are described below in the context of an application involving drainage of fluids from a surgical site, but those of skill in the art will appreciate that the present invention is not so limited. For instance, embodiments of the present invention may be used in any suitable medical application involving the use of a catheter, including but not limited to thoracic drains, feeding tubes, venous catheters (PICC, midline, and central line), peritoneal dialysis catheters, and percutaneous urinary catheters. Correspondingly, embodiments of the invention are not limited to the catheters shown in the Figures, and instead they may employ catheters of any type used in any medical application. Thus, the term "catheter" as used herein refers to a flexible, tubular medical device that is insertable into a human body for withdrawal of fluids from or introduction of fluids into the body. As those skilled in the art will appreciate, a portion of the catheter (such as the portion to be inserted in a body passage) may be perforated (see FIGS. 10A-17C) to allow for ingress and/or egress of fluids.

Turning now to FIGS. 3-4, an embodiment of an anchor assembly 100 is illustrated secured to a patient's skin 102 (FIG. 3) and prior to use (FIG. 4). In this regard, anchor assembly 100 comprises an anchor 104 that is coupled with a catheter 106. In this embodiment, as explained in greater detail below, catheter 106 is removably attached with anchor 104 and only one catheter 106 is provided in anchor assembly 100, but neither is required in all embodiments. Additionally, as seen in FIG. 3, anchor assembly 100 comprises an adhesive dressing 108 that is configured to affix anchor 104 in place against skin 102 and to reduce and/or prevent movement of catheter 106 once inserted in a body passage. Although not illustrated in the figures, in various embodiments, an anchor assembly 100 may also include a fluid collection bulb or other collection apparatus that is in fluid communication with a distal end of catheter 106.

In the illustrated embodiment, anchor 104 comprises an anchor body 110, which as shown may be generally dome-shaped, though this is not required in all embodiments. A flange 112 depends from anchor body 110 and, in use, flange 112 is in engagement with skin 102. Also, a coupling 114 projects from anchor body 110. As described in more detail below, in use, coupling 114 receives catheter 106 and secures catheter 106 with respect to anchor body 110. In some embodiments, anchor body 110 may also define a cavity 116 therein that facilitates application of a topical therapeutic in a variety of mediums.

Preferably, anchor 104 is flexible and may be formed from one or more thermoplastic or elastomeric material(s). As those of skill in the art will appreciate, a variety of thermoplastic or elastomeric materials are suitable for use in forming anchor 104 and are contemplated for use in various embodiments. For instance, liquid silicone rubber (LSR), Viton® fluoroelastomer (FKM), and ethylene propylene (EPDM) are examples of medical-grade elastomers that may be used, and examples of thermoplastics that may be suitable include thermoplastic polyurethane (TPU), polypropylene, polymethyl methacrylate (PMMA), polyvinyl chloride (PVC), polyamide (nylon), acrylonitrile butadiene styrene (ABS), and polycarbonate (PC). In one embodiment, anchor 104 may be formed from medical grade silicone. Anchor 104 (and other embodiments of anchors and fittings, hose barbs, etc., described herein) may be manufactured using any suitable method, such as via injection molding. Catheters 106 may be formed via an extrusion process in various embodiments.

In various embodiments, anchor body 110, flange 112, and coupling 114 may be integrally-formed or may each be separate components that are coupled together. Additionally, while certain illustrated embodiments show anchor 104 retaining a single catheter, those of skill in the art will understand in view of the present disclosure that embodiments of the present invention also include multi-tube anchors. Thus, in some embodiments where a single anchor is used to retain multiple catheters, more than one coupling 114 may project from body 110, or more than one body 110 and projecting coupling 114 may be provided.

As shown, flange 112 may be generally annular in shape, though in other embodiments flange 112 may take any suitable shape. For instance, rather than being circular as shown, the periphery of flange 112 may be square or triangular in some embodiments. Also, where an anchor is configured to secure more than one catheter tube, the flange 112 may be, for example, pill-shaped. In embodiments where cavity 116 is provided, such as the embodiment illustrated in FIG. 4, flange 112 may define an internal diameter that is equal to the diameter of the opening of cavity 116. In certain embodiments where cavity 116 is not provided, an opening may nonetheless be defined in flange 112 to allow passage of catheter 106.

As those of skill in the art will appreciate, flange 112 operates to move the retention stress of the attachment to the skin radially away from an incision through which catheter 106 passes. This may reduce patient pain and discomfort. Flange 112 may also assist in "sealing" an incision or entry point from atmospheric bacteria. In some embodiments, it is contemplated that flange 112 could be adhered to skin 102 via surgical glue, double-sided tape, or another suitable attachment mechanism. In certain embodiments, however, no adhesive is disposed between the patient's skin 102 and the skin-facing side of flange 112. Rather, as described in more detail herein, an adhesive dressing 108 disposed over the exterior-facing side of flange 112 and which adheres to the skin only at locations beyond the outer periphery or diameter of flange 112 may be used.

As noted above, although not provided in all embodiments, in this embodiment anchor 104 comprises a cavity 116 defined in anchor body 110. Cavity 116 may operate as a time-release topical therapeutic or salve reservoir in some embodiments. In various embodiments, a physician installing anchor 104 may dispose or apply antiseptics, antibiotics, pain medication, moisturizer, or another topical therapeutic or the like in cavity 116 prior to securing anchor 104 to the patient. In other embodiments, anchor assembly 100 may have any suitable topical therapeutic pre-loaded in cavity 116 and sealed with a removable liner. The topical therapeutic may inhibit infection, reduce pain, and/or keep the skin 102 from drying out or forming scar tissue. Those of skill in the art can define the interior volume of cavity 116 as appropriate to the application for which anchor 104 is to be used. For instance, the interior volume of cavity 116 may be selected to hold enough of the desired topical therapeutic to be applied or used over a predetermined period of time, such as the amount of time that the catheter is to remain installed in the patient's body.

With reference also to FIGS. 5-8, the topical therapeutic may be placed in cavity 116 in liquid, solid, gel, or impregnated sponge forms. For example, FIGS. 5-7 illustrate the use of an impregnated sponge 118 that is disposed in cavity 116. Sponge 118 may have an annular shape and define an opening therethrough that is sized to be received over catheter 106. Likewise, the outer diameter of sponge 118 may be about the same size as or slightly smaller than the internal diameter of cavity 116. In some embodiments, sponge 118 may be impregnated with an active ingredient of chlorhexidine, and it may for example be analogous to the BioPatch R product offered by Ethicon, Inc. of Somerville, NJ. In various embodiments, sponge 118 may define a slit extending between the inside and outside diameters to facilitate installation around catheter 106, but this is not required. FIG. 8 illustrates the use of a gel 120 disposed in cavity 116. Gel 120 may, for example, comprise active ingredients such as neomycin, polysporin, and/or bacitracin, and gel 120 may, for example, be analogous to the NeosporinR product offered by Johnson & Johnson Inc. of New Brunswick, NJ. Another example of a topical therapeutic is colloidal silver.

In this embodiment, coupling 114 comprises a length of flexible, thin-wall tubing having a proximal end 122 and a distal end 124. Coupling 114 defines a bore 126 (see, e.g., FIG. 4) therethrough extending between the proximal and distal ends 122, 124. The internal diameter of bore 126 is sized to receive catheter 106 therethrough, and it may vary depending on the type of catheter 106 used or the medical application. In embodiments where cavity 116 is provided, bore 126 opens into cavity 116. In other embodiments, bore 126 may open to the skin-facing side of flange 112. In this embodiment, coupling 114 projects from anchor body 110 in a generally lateral direction, though this is not required in all embodiments. In some embodiments, coupling 114 may define a longitudinal axis that is parallel with or at an angle relative to the plane in which flange 112 lies. In some embodiments, it is preferred that coupling 114 project from anchor body 110 in a direction that is generally parallel with flange 112 so that, when anchor assembly 100 is used on a patient, distal end 124 of coupling 114 may be oriented toward the patient's feet. That way, when the patient stands and the anchor 104 is supporting the weight of the assembly 100, the catheter 106 will not kink and suffer a restriction in flow.

In general, catheters formed from silicone or similar materials are particularly difficult to grip without crimping or constricting the flow therethrough. As noted above, presently-available systems and methods for anchoring a catheter to the skin rely upon cinching a suture, cable tie, narrow band, or the like around the catheter to facilitate attachment. In contrast, embodiments of the present invention contemplate several methods by which a catheter may be secured with respect to an anchor and, thus, to the patient's skin, without constricting flow therethrough.

In some embodiments, a catheter may be pre-attached to an anchor, for example during manufacturing, to ensure a robust attachment. The catheter may be attached to the anchor via surgical glue or silicone-based glue or another suitable adhesive. In other embodiments, the catheter may be chemically bonded to the anchor via a suitable solvent. In still other embodiments, an example of which is shown below, the anchor may be over-molded on the catheter. In still other embodiments, the catheter may be divided into an inner, or internal, catheter and an outer, or external, catheter. Either or both of the internal and external catheters may be integrated with or removably attachable to the anchor or a fitting disposed (or molded) therein. Various examples of these embodiments are also discussed in more detail below.

In the illustrated embodiment, however, catheter 106 is not pre-attached to anchor 104 and instead is removably attached thereto by passing through bore 126 defined in coupling 114. In this regard, coupling 114 may act as an extended "friction sleeve" and may have an internal diameter selected to apply a compression force to the catheter 106 to be used in the particular application. The compression force creates enough friction between the coupling 114 and catheter 106 to hold catheter 106 securely within anchor body 110. The length of coupling 114 is selected to ensure that the compressive force is evenly distributed and does not crimp catheter 106 or reduce its inside diameter. Therefore, catheter 106 will not restrict the flow of fluid in bore 126 or catch solids therein.

In contrast to known anchor devices wherein the anchor is clipped onto a catheter after the catheter is installed in a patient's body, in this embodiment, a surgical tech or surgeon may attach the catheter 106 to the anchor 104 before catheter 106 is installed in the patient's body. As noted above, this also could be done at a factory or during manufacturing. In this manner, the catheter may be installed in a "retrograde" fashion (i.e., from the outside of the patient's skin into the surgical site or body passage) in some embodiments and some medical applications. As those of skill in the art will appreciate, even though the catheter insertion site will have been disinfected (e.g., via clorohexadine) prior to an incision being made, there is still a minute possibility that a small amount of bacteria is still on the skin and could be transferred from the skin to the catheter tube where retrograde installation is used. If that were to happen, the bacteria could be transferred deep into a body passage or surgical site and may increase the chances of an infection developing. Accordingly, in some embodiments, it is contemplated that an antibiotic and/or antimicrobial coating is applied to the exterior of the end of the catheter that will be inserted into the patient's body. Those of skill in the art are familiar with antibiotic and antimicrobial coatings that are suitable for this purpose. Alternatively, in some embodiments, an antimicrobial agent, such as but not limited to silver, is impregnated into the elastomer used to extrude the catheter.

Alternatively, in the illustrated embodiment and/or in embodiments where a detachable internal catheter is provided, the catheter may be installed in anterograde fashion (i.e., from within the surgical site/body passage outward through the patient's skin). In other words, in some embodiments, it is contemplated that the surgical tech or surgeon may install the catheter (or, where divided, only the internal catheter) first and then attach the anchor thereto and adhere the anchor to the patient's skin.

In any event, in embodiments where cavity 116 is provided, it will be appreciated from the above discussion that catheter 106 may pass through cavity 116. The cavity 116 thus may surround catheter 106 at the point of insertion of catheter 106 in the patient's skin. Thus, the incision or other entry point may be immersed in topical therapeutics.

In various embodiments, and as needed for various applications, anchor 104 may have various different sizes. In one example embodiment that may be used in a surgical drain application, flange 112 of anchor 104 may have an outside diameter of about 40 mm and an inside diameter (e.g., at the opening of cavity 116) of about 20 mm. In some embodiments, the inside diameter of flange 112 on its skin-facing side is about the same as the inside diameter on the exterior-facing side (taking into account the thickness of anchor body 110), and as such, the outer diameter of anchor body 110 may be about the same as or slightly larger than the outer diameter of cavity 116. Of course, in other embodiments, the anchor body 110 may have different peripheral dimensions and/or a different shape than cavity 116. Additionally, in this example embodiment, the length of coupling is about 25 mm, and the coupling has an internal diameter (e.g., the diameter of bore 126) of about 4.95 mm, while the catheter 106 has an outside diameter of about 5 mm. Thus, in this embodiment, there is about a 0.05 mm interference between the two components, but in other embodiments, the amount of interference could be increased, and/or the coupling length could be increased. In such embodiments, the frictional retention of catheter 106 in coupling 114 would be increased. Also, those of skill in the art will appreciate that certain standard catheters have outside diameters ranging in size between 1 mm and 11.33 mm, and as such, depending on the medical application and the type of catheter used, the inside diameter of coupling 114 will vary accordingly.

As noted above, in various embodiments, anchor assembly 100 may comprise an adhesive dressing that is configured to secure anchor 104 to the patient's skin. In FIG. 4, adhesive dressing 108 is shown after attachment to the patient's skin 102. However, adhesive dressing 108 may comprise a plurality of layers, including adhesives, one or more removable liners, and one or more application layers, that are removed and/or applied during catheterization. Thus, in accordance with one embodiment, FIG. 9 illustrates an adhesive dressing 150 that may be used with embodiments of anchor assembly 100.

Turning to FIG. 9, two exploded views of adhesive dressing 150 are shown on the right and left-hand sides of the Figure. In general, adhesive dressing 150 in this embodiment comprises an adhesive layer 152. Adhesive layer 152 as shown is annular in shape and comprises a top side 154, a bottom side 156, and defines a central aperture 158. As described in more detail herein, this shape allows the adhesive layer 152 to overlay flange 112 of anchor 104 and trap flange 112 against the patient's skin. This provides a very strong connection with the patient's skin while also allowing the anchor body 100, coupling 114, and catheter 106 to pass through the center of adhesive layer 152.

In general, and referring again to FIG. 4, adhesive layer 152 is sized to be secured to an area of the skin that surrounds flange 112. Thus, in various embodiments, adhesive layer 152 may have a diameter or area (where layer 152 does not have a circular periphery) that is about 1.5 times the diameter or area of flange 112, about 2 times the diameter or area of flange 112, about 2.5 times the diameter or area of flange 112, and/or about 3 times the diameter or area of flange 112. Of course, it is contemplated that adhesive layer 152 may have any suitable diameter or area, including other diameters or areas than those explicitly mentioned, as needed or desired for particular applications. Using the example mentioned above, where flange 112 is annular in shape and has an outside diameter of about 40 mm, adhesive layer 152 also is annular and has an outside diameter of about 80 mm in this example. The diameter or area/shape of central aperture 158 may correspond to the diameter or area/shape of anchor body 110, such that adhesive layer 152 may be received thereover. In various embodiments, the diameter or area of central aperture 158 may be about the same as the diameter of area of the periphery of anchor body 110, and thus as shown in FIG. 9, the diameter of central aperture 158 may be about 20 mm. However, in some embodiments, the diameter or area of central aperture 158 may be slightly larger than the diameter of area of the periphery of anchor body 110, as long as the adhesive layer 152 still adheres to enough of the exterior-facing side of flange 112 to secure flange 112 against the patient's skin.

Adhesive layer 152 may be formed of a thin elastic layer (e.g., of polyurethane or the like) and comprises a suitable medical adhesive on bottom side 156 thereof to engage the patient's skin. Those of skill in the art are familiar with a variety of suitable materials that may be used for adhesive layer 152. In general, the material selected for adhesive layer 152 should be flexible and contour to the compound curves of a patient's body. Likewise, the material selected preferably provides an adhesive that allows adherence to a patient's skin for the duration of the period of catheterization, such as more than seven (7) days even with sweat and showers. Further, it is contemplated that, in some embodiments, adhesive layer 152 may be analogous to the polyurethane material used in the DermaMed Coatings Company LLC (Tallmadge, Ohio) product number DM-4034. In other embodiments, adhesive layer may be similar to the transparent dressings used in the TegadermR line of products offered by 3M, of Maplewood, Minnesota.

In this embodiment, adhesive dressing 150 also comprises an application layer 160. Here, application layer 160 is disposed above and removably coupled with top side 154 of adhesive layer 152. In some embodiments, application layer 160 may be removably coupled with top side 154 via low-tack adhesive or the like. Application layer 160 may be any suitable backing layer that provides structure to adhesive layer 152 during application, and it may take any shape, though the shape of application layer 160 preferably corresponds to the shape of adhesive layer 152. Application layer 160 also is generally annular in shape and defines a central aperture 164, which may be in registration with and have the same or similar diameter or area as central aperture 158. As described in more detail below, application layer 160 defines a radial slit 162 in this embodiment that extends between the peripheral edge of layer 160 and aperture 164. Where slit 162 is provided, it permits catheter 106 to slide out of aperture 164 to the peripheral edge of layer 160 quickly and easily after adhesive layer 152 is attached to the patient's skin. However, slit 162 is not required in all embodiments, and where slit 162 is not provided, application layer 160 can still be removed after adhesive layer 152 is attached to the patient's skin by sliding application layer 160 along the length of catheter 106. Notwithstanding the above, in some embodiments, adhesive dressing 150 does not comprise an application layer 160. For instance, depending on the thickness and rigidity of adhesive layer 152, in some embodiments application layer 160 is not required to keep adhesive layer 152 from folding over on itself during installation. Still, in certain embodiments the use of an application layer 160 may be preferred so that adhesive layer 152 can be thinner, more supple, and/or more breathable.

Further, adhesive dressing 150 comprises a removable liner layer 166 that is disposed on bottom side 156 of adhesive layer 152. Liner layer 166 covers the adhesive on bottom side 156 prior to use of adhesive dressing 150, and it may be removed during application of anchor 104 as described in more detail below. Like application layer 160, liner layer 166 may be any suitable shape, though it preferably corresponds in shape to that of adhesive layer 152. Here, liner layer 166 is generally annular in shape and defines a central aperture 168. The diameter or area of central aperture 168 may correspond to or be slightly larger than the outer diameter or peripheral edges of flange 112, and thus central aperture 168 in this embodiment is larger than central apertures 164, 158. Also like application layer 160, liner layer 166 defines a slit 170 extending between the periphery of liner layer 166 and central aperture 168.

As those of skill in the art will appreciate, ease of use is critical to the successful adoption of products in general and even more so with surgical products. A surgeon should be able to install an anchor (or anchor assembly) quickly and properly with little to no practice. Therefore, a design making the removable liners and application layers intuitive and simple to use, such that when applied the dressing lays down flat with no folds or wrinkles, is important. Embodiments of the inventive design preferably allow the surgeon or surgical tech to remove each layer with one motion of one hand. Thus, in the illustrated embodiment, liner layer 160 defines a pull tab 169 and liner layer 166 defines a pull tab 171. Pull tabs 169, 171 may extend beyond the outer diameter of adhesive layer 152 opposite the locations of catheter 106 on either side of anchor 104. Slits 162, 170 allow the layers 160, 166 to release around the catheter as it is pulled away.

Additionally, in some embodiments, a second liner layer 172 may be provided to cover the skin-facing side of flange 112. Second liner layer 172 may therefore have the same basic shape and dimensions as that side of flange 112, and second liner layer 172 may be formed of the same material or a different material than liner layer 166. Second liner layer 172 may be removable with (e.g., attached by perforations or integral with) liner layer 166, or second liner layer 172 may be separately removable in some embodiments. In various embodiments, second liner layer 172 may comprise adhesive on the surface thereof that engages flange 112 to secure second liner layer 172 in place against flange 112 until removal is required. Further, second liner layer 172 may be annular in shape in some embodiments and may define a central aperture 174. The diameter or area of central aperture 174 preferably corresponds to the outside diameter or peripheral edges of cavity 116 (where provided), though central aperture 174 is not required in all embodiments.

In embodiments where cavity 116 is provided and is pre-filled with a topical therapeutic, and either in lieu of or in addition to second liner layer 172, adhesive dressing 150 may comprise a liner layer 176 (FIG. 10). In this embodiment, liner layer 176 is sized and shaped to cover flange 112 and the opening of cavity 116, though in other embodiments, liner layer 176 may be larger or smaller as needed or desired. Liner layer may also define a central aperture 178 having an inside diameter that is selected to create a slight interference fit with the outside diameter of catheter 106. As will be appreciated, catheter 106 extends through central apertures 164, 158, 168, and 178. Due to the dimensions of catheter 106 and central aperture 178, liner layer 176 may seal any pre-filled topical therapeutic in place in cavity 116. In some embodiments, liner layer 176 may comprise a layer of adhesive 180 configured to releasably seal liner layer 176 to flange 112 of anchor 104. As shown, adhesive 180 may, for example, be arranged in an annular fashion dimensioned to correspond to the dimensions of flange 112. Also, like liner layers 160, 166 described above, liner layer 176 may also define a pull tab 182 in some embodiments.

Embodiments of the present invention also provide various methods. Examples of the methods performed in accordance with embodiments of the present invention are provided herein. One such method is described below with reference to FIGS. 10A-12C. In this embodiment, the method employs anchor assembly 100, including adhesive dressing 150 as modified with liner layer 176. However, upon review of other anchor assembly embodiments described herein, those of skill in the art will appreciate and understand other methods that may employ such other anchor assembly embodiments. Such other methods are expressly contemplated and within the scope of the present invention.

Turning to FIGS. 10A-12C, the method begins. At the first step, as shown in the perspective view of FIG. 10A, an anchor assembly 100 is provided. As shown in FIGS. 10B and 10C, at the second step, the liner layer 176 is removed. For example, a user may grasp pull tab 182 and thread liner layer 176 over catheter 106 to expose flange 112 and cavity 116. Next, as shown in FIG. 11A, a portion of catheter 106 is partially inserted percutaneously into a body passage or surgical site. Then, as shown in FIG. 11B, liner layer 166 is removed. For instance, a user may grasp pull tab 171 and pull liner layer 166 away from back side 156 of adhesive layer 152. Slit 170 allows the liner layer 166 to be pulled around catheter 106 and away from anchor assembly 100 for disposal. With reference to FIGS. 12A-12C, at the next step, adhesive layer 152 and, thus, anchor assembly 100, is adhered to the patient's skin 102. At this point, the internal portion of catheter 106 is fully within the body passage or surgical site. Then, as shown in FIG. 12B, application layer 160 is removed. For example, a user may grasp pull tab 169 and pull application layer 160 away from top side 154 of adhesive layer 152. Slit 162 allows application layer 160 to be pulled around the external portion of catheter 106 and away from anchor assembly 100 for disposal. Thereafter, the catheter 106 is securely held in place on a patient's skin via anchor 104 and adhesive layer 152, and the method ends.

Certain additional embodiments of the invention are discussed with reference to FIGS. 13A-17. The embodiments illustrated in these figures are analogous in certain respects to the embodiments described above in reference to anchor assembly 100. Where that is the case, like reference numerals are used to denote like parts.

As noted above, embodiments of the invention include various methods for attaching a catheter to an anchor. First, with reference to FIGS. 13A and 13B, an anchor assembly 200 is illustrated. Anchor assembly 200 is in many respects similar to anchor assembly 100, described above, except in this embodiment, anchor 104 is over-molded with a single-piece catheter 106. This is best seen in the cross-sectional view of FIG. 13B.

Next, as noted above, in certain embodiments, the catheter may be divided into two or more pieces. One such embodiment is illustrated with reference to FIGS. 14A-15E, which illustrate components of an anchor assembly 250. Here, anchor assembly 250 comprises a flexible elastomeric anchor 252 (FIGS. 15A-15E). In general, anchor 252 is analogous to anchor 104, described above, except with regard to coupling 114. Rather than a tube projecting from body 110, a fitting 254 is disposed within bore 126, and catheter 106 is divided between an internal catheter 256 and an external catheter 258.

Fitting 254, which may be rigid or flexible and formed of any suitable material, may be similar in shape to a 90-degree elbow fitting in some embodiments, though fitting 254 may be straight or define other angles in other embodiments. In general, fitting 254 comprises a tube having an internal bore 260 through which fluid 260 may pass between internal and external catheters 256, 258. At each end thereof, fitting 254 comprises catheter connection members, such as barbs 262 configured to receive and retain catheters 256, 258 thereon. As those of skill in the art will appreciate, barbs 262 may comprise a plurality of annular projections from the tube ends of fitting 254 that have an outside diameter that is greater than the inside diameter of catheters 256, 258. In other embodiments, however, other catheter connection members may be used. In various embodiments, fitting 254 may be molded into or with anchor 252, though fitting 254 also could be glued, bonded, or friction retained in anchor 252. Fitting 254 and/or barbs 262 may also be formed of a metal material, such as stainless steel or titanium, in some embodiments.

Other embodiments are contemplated. For example, an anchor in accordance with one embodiment may comprise a fitting that has only one connection at which one side of a divided catheter is removably connected, and the other side of the divided catheter may be integrated into (e.g., over-molded with) the anchor. Additionally, in some embodiments, use of a divided catheter may allow for a fitting internal to the anchor that comprises one or more valves. For example, while any suitable valve may be provided in various embodiments, it is contemplated that, in some embodiments, a check valve may be used. In a surgical drain application, for example, the check valve may operate to ensure that no air or fluid is sucked back into the surgical cavity if the drain bulb loses suction. Again, any type of check valve may be used. In the embodiment shown in FIGS. 16A-17C, however, the check valve comprises a ball check valve.

More particularly, FIGS. 16A-17C illustrate an anchor assembly 300 in accordance with an embodiment of the present invention. In this embodiment, anchor assembly 300 comprises an anchor 302. Anchor 302 in this embodiment comprises an anchor body 304 having a depending flange 306 and an opening 308. In this embodiment, an internal catheter 310 is integral with anchor body 304, as best seen in FIGS. 17B and 17C, at a floor 312. In various embodiments, internal catheter 310 may be injection molded with anchor body 304 or it could be extruded, perforated, then over-molded with anchor body 304. Anchor body 304 defines a first cavity 314 within which a fitting 316 is disposed. Anchor body also defines a second cavity 318 surrounding catheter 310 that may be used as a topical therapeutic reservoir.

Here, fitting 316, which again may be rigid or flexible, comprises a tube 320 having at one end thereof a catheter connection member 322 (e.g., barbs) and at the other end thereof a ball check valve 324. An external catheter 258 is connectable at catheter connection member 322 and is this able to be in fluid communication (via fitting 316) with internal catheter 310. Ball check valve 322 may comprise a ball that is biased via a spring (FIG. 17C) to a normally-closed position. As shown in FIG. 17B, in the presence of outward flow, fluid flowing from internal catheter 310 to external catheter 258 forces the ball against the spring, causing the check valve to open. As shown in FIG. 17, in the event of inward flow (i.e., from external catheter 258 to internal catheter 310), the check valve is closed due to the spring biasing the ball against its seat at the opening of internal catheter 310.

Additional embodiments of the present invention are discussed in connection with FIGS. 18-22B. More particularly, FIGS. 18-19E depict an anchor assembly 400 in accordance with one embodiment. In general, anchor assembly 400 comprises an anchor 402 coupled with a drain tube 404 having a perforated end 406. As described in more detail below, an adhesive subassembly 408 is coupled with anchor 402. FIG. 20 is an exploded view of adhesive subassembly 408, and FIGS. 21A-E are various views of anchor 402. FIGS. 22A-B are views of anchor 402 coupled with drain tube 404. An example method of assembling adhesive subassembly 408 with anchor 402 also is described below.

Turning first to FIGS. 21A-E, in one embodiment, anchor 402 comprises an anchor body 410 coupled with an annular flange 412. In this embodiment, anchor 402 is not provided with a cavity such as that described above. Rather, anchor body 410 defines an internal bore, or sleeve, 414 sized to received a suitable catheter or drain tube therein. Bore 414 extends through anchor body 410 between flange 412 and a distal end 416 of body 410. As shown, anchor body 410 may be arcuate and flange 412 may be annular in shape, though this is not required, and other shapes are within the scope of the present invention. The portion of bore 414 at distal end 416 of body 410 may define a longitudinal axis A (FIG. 22B) that extends parallel with flange 412, though this too is not required. Anchor 402 preferably is formed of a suitable elastomeric material, such as medical grade silicone rubber. In one embodiment, flange 412 may have an outer diameter of about 25 mm, bore 414 may have an internal diameter of about 4.9 mm (e.g., for an interference fit with a tube having an outside diameter of 5.0 mm), and the lengthwise distance between the center of the opening of bore 414 in flange 412 and the distal end 416 of body 410 may be about 23.6 mm. Also, in one embodiment, the portion of bore 414 at its opening to flange 412 may define a longitudinal axis B (FIG. 22B), and the angle between axes A, B may be approximately 110 degrees. Of course, all dimensions are exemplary and a skilled artisan can select other suitable dimensions, as needed or desired for various applications.

FIGS. 22A-B are views of anchor 402 coupled with drain tube 404 when the adhesive subassembly is not 408 is not yet assembled with anchor 402. In various embodiments, drain tube 404 may be friction fit with anchor 402 or anchor 402 may be molded over or bonded to anchor 402, as described above. Drain tube 404 may be analogous to catheter 106 described above, but in various embodiments, drain tube 404 may be any suitable surgical tubing (optionally including perforated end 406) formed, for example, of medical grade silicone rubber. For instance, Drain tube 404 may be similar to the wound drains offered by Medline Industries, Inc. of Northfield, IL in some embodiments.

Turning now to FIG. 20, adhesive subassembly 408 in various embodiments comprises a plurality of layers. In the illustrated embodiment, adhesive subassembly 408 comprises a dressing 418 having a first side 420 and an opposite second side 422. As those of skill in the art will appreciate, dressing 418 may be used to secure anchor 402 and flange 412 against the skin of a patient. Second side 422 may comprise a suitable adhesive, and a removable installation liner 424 may be disposed against and cover second side 422 to protect the adhesive until the anchor assembly 400 is to be used. In this embodiment, dressing 418 defines a central aperture 426, and liner 424 defines a central aperture 428. As shown, apertures 426, 428 are in alignment.

Dressing 418 in various embodiments may be any suitable flexible adhesive dressing. As those of skill in the art will appreciate, dressings that are thick and/or rigid may cause patients to develop blisters around the edges where dermal layers are caused to delaminate by shear forces. In one embodiment, dressing 418 may comprise a transparent film (e.g., polyurethane) dressing. Dressing 418 may be approximately 0.08 mm thick, and it too may be similar to the transparent dressings used in the TegadermR line of products offered by 3M, of Maplewood, Minnesota. Liner 424 may be any suitable liner for an adhesive dressing. In one embodiment, installation liner 424 may comprise a white paper liner that defines a pull tab 430 and a perforation or slit 432 that allows liner 424 to be removed around a drain tube 404 that may have already been inserted into a patient.

In various embodiments, the adhesive of dressing 418 must be sufficiently adhered to the patient's skin. It has been found, however, that physicians may not apply sufficiently even compressive forces over the adhesive surface area to wet-out the adhesive and chemically bond the dressing to the patient's skin across the whole surface area of the substrate. For instance, a physician may use her fingertips to compress an adhesive dressing against a patient's skin for a second, reposition her fingers and compress for a second, and so on, continuing this process for about 10 seconds to try to compress the whole surface area of the dressing. In essence, these are point loads that are applied for a second or two, when a sufficient attachment may instead require 10-30 seconds of even compression over the entire surface area of the adhesive dressing. As a result, some adhesive dressings may not adhere well to a patient's skin. Accordingly, in some embodiments of anchor assemblies disclosed herein, a semi-rigid compression layer may be provided to distribute the force from the physician's fingertips to the whole adhesive area without the need for the physician to reposition her fingers.

For example, in the illustrated embodiment, subassembly 408 may comprise a removable application layer 434. Application layer 434 may be any suitable semi-rigid or rigid material, such as a clear plastic layer formed, for example, from PET or the like. A material having some flexibility may allow the application layer 434 to roll off of the dressing 418 more easily when the application layer 434 is being removed, as described below, whereas a more rigid layer may pull the adhesive off of the skin when attempting to remove the application layer 434.

In various embodiments, application layer 434 may be manufactured together with dressing 418 and liner 424. For example, application layer 434 may be bonded with dressing 418 via static electricity. In some embodiments, application layer 434 may have a thickness of about 0.08 mm. In some embodiments, application layer 434 may be referred to as a casting or casting layer.

Application layer 434 may also define a central aperture 436 and a perforation or slit 438. Again, perforation or slit 438 permits application layer 434 to be removed around a drain tube that may be extending from anchor 402. In use, aperture 436 may also be aligned with apertures 426, 428.

Additionally, subassembly 408 may comprise a compression layer 440 that may be coupled with application layer 434 via a suitable adhesive layer 442. Compression layer 440 and adhesive layer 442 may each be annular in shape with respective central apertures 444, 446. Apertures 444, 446 also may be aligned with apertures 426, 428, and 436 in use. Compression layer 440 may have a first side 441 and an opposite second side 443, and adhesive layer 442 may have a first side 445 and an opposite second side 447. As shown, each of layer 440 and adhesive layer 442 may define a peripheral slot or opening 448, 450, respectively. As described in more detail below, slots 448, 450 may be sized to receive a portion of anchor body 410 therethrough, and slots 448, 450 also facilitate removal of compression layer 440 and adhesive layer 450 around anchor body 410 and any attached drain tube.

In various embodiments, compression layer 440 may be formed of any suitable semi-rigid compressive material. For instance, a 0.5 mm plastic sheet, card stock, or cardboard could be used. In the illustrated embodiment, compression layer 440 is formed from a low density closed-cell foam rubber material, and it may be about 12 mm thick. Adhesive layer 442 may comprise a double-sided adhesive tape analogous to the 300LSE adhesive tape offered by 3M, though other suitable adhesives may be used. As is understood, removable liner layers (not shown) may protect the adhesive on each side 445, 447 of adhesive layer 442 until it is used.

As described further herein, in use, a physician may apply pressure to layer 440 to cause dressing 418 to be adhered to a patient's skin and to confine anchor 402 against the skin with drain tube 404 inserted therein. Because of application layer 434, which is aligned with and overlies dressing 418, force from the physician's fingertips on layer 440 is distributed and applied evenly to the whole adhesive area on the second surface 422 of dressing 418. In various embodiments, for example, compression layer 440 with a few fingers for 10-30 seconds evenly wets out the whole adhesive area for that whole time, resulting in a much stronger bond with the patient's skin. Additionally, compression layer 440 may then be used as a "handle" for removing application layer 418.

As noted above, in some embodiments, anchor 402 is formed of silicone rubber. Few, if any, adhesives can form a strong bond with this material, and so in various embodiments, the adhesive dressing is received over anchor 402 and adhered primarily to the patient's skin around anchor 402. Again, a thinner dressing typically is preferred to avoid blistering. But because the silicone rubber material does not form a strong bond with the adhesive on the dressing, and because in a thinner adhesive dressing it is more likely that an internal aperture can stretch open wider, it is possible in some implementations for the flange 412 to fold and be pulled through the internal aperture when a force is applied. This may result in the drain tube 404 being removed from the surgical site, and a new dressing and tube insertion may be required. While thicker, more rigid dressings that have central apertures with a tight inside diameter could be used, this risks blistering on a patient's skin. Depending on the application, anchor 402 could be formed from an elastomeric material other than silicone rubber that adheres better with the adhesive on the dressing, but those of skill in the art will appreciate that silicone rubber is frequently used where contact with body fluids is required.

Thus, in the illustrated embodiment, adhesive subassembly 408 also comprises a collar 452 that may be used to reinforce flange 412 so that a thinner, more flexible adhesive dressing 418 and/or a silicone rubber anchor 402 may be used, and blistering on a patient's skin will be less likely to occur. More particularly, collar 452 is configured to be adhered to the adhesive on dressing 418 and to be received over anchor body 410. Thus, in general, the dimensions and shape of collar 452 may be complementary to those of anchor body 410, and collar 452 may be formed from a suitably rigid material that will not stretch to an extent that flange 412 is allowed to be pulled therethrough. Collar 452 may also be formed of a material that forms a strong adhesive bond with the second side 422 of dressing 418.

In this embodiment, collar 452 is annular in shape and defines a central aperture 454. Collar 452 is formed of a thermoplastic polymer material, such as polycarbonate or PET. As described in more detail below, installation liner 424 may also comprise one or more central liners that are separately removable from installation liner 424, such as a collar liner 456 and a flange liner 458. Collar liner 456 may have the same or similar dimensions to collar 452, and thus it may extend between central aperture 428 and a diameter corresponding to the outside diameter of collar 452. There, a perforation or slit may be formed. Flange liner 458 may have the same or similar outer dimensions to flange 412 of anchor 402, and thus flange liner 458 may extend from collar liner 456 to a diameter corresponding to the outside diameter of flange 412. In other embodiments, a single central liner could be provided, such as a central liner that extends from central aperture 428 to a diameter that corresponds to the outside diameter of flange 412. In any event, as described below, either or both liners 456, 458 may be removed separately from (e.g., prior to removal of) installation liner 424 so that collar 452 may be secured to the underside of dressing 418 before anchor 402 is inserted through central apertures 428, 426, 436, 444, and 446. When anchor 402 is inserted, collar 452 will be received over anchor body 410.

A skilled artisan can select suitable dimensions for adhesive subassembly 408 in various embodiments. Preferably, apertures 426, 428, 436, 454 preferably are sized to receive anchor body 410 therethrough but are smaller than the diameter of flange 412. For instance, these apertures may have an internal diameter of 10 mm in some embodiments. The outside diameter of dressing 418 in subassembly 408 preferably is larger than the diameter of flange 412 by a sufficient amount to allow for a good connection between the second side 422 and the patient's skin, as described herein. In some embodiments, the outside diameter of dressing 418 may be about 50 mm. The outside diameters of layers 424, 434, 440, 442 may be the same as that of dressing 418. In some embodiments, the internal diameter of apertures 444, 446 may be 26 mm. In some embodiments, the outside diameter of collar 452 may be about 18 mm, and collar 452 may be formed of 4 mil PET. Again, though, all dimensions and materials are exemplary, and a skilled artisan can select other suitable dimensions and materials, as needed or desired for various applications.

Finally, in various embodiments, anchor subassembly 408 may comprise one or more stickers 460, 462 on which indicia may be provided to provide visual aids to the physician during use. For example, sticker 460 may be disposed on compression layer 440, and sticker 462 may be disposed on installation layer 424. As shown in FIG. 20, for example, indicia 464 is provided on sticker 460 in the form of the number "2" and arrows. Similar indicia, e.g., in the form of the number "1" and arrows, could be provided on the underside sticker 462, which is not shown. These indicia may indicate the order in which various layers are to be used. In that regard, in use, a physician may first remove the installation liner 424, and after the adhesive dressing is placed against a patient's skin, the physician may then apply pressure to compression layer 440. In other embodiments, of course, any suitable indicia may be provided.

A method of assembling a surgical drain according to one embodiment also is provided. Again referring to FIGS. 18-22B, at the outset, installation liner 424, dressing 418, and application layer 434 may be provided and/or manufactured as a single subassembly or unit. In this subassembly, liner layer 424 may be adhered to second side 422 of dressing 418, and application layer 434 may be suitably coupled to first side 420 of dressing 418. Sticker 462, if provided, may be attached to the side of installation layer 424 opposite dressing 418. Likewise, compression layer 440 and adhesive layer 442 may be provided and/or prepared as a single subassembly or unit. In this subassembly, the first side 445 of adhesive layer 442 may be adhered to second side 443 of compression layer 440, and a removable liner may be provided on second side 447 of adhesive layer 442. If provided, sticker 460 may be applied to the surface of compression layer 440 opposite adhesive layer 442.

Then, the liner on second side 447 of adhesive layer 442 may be removed, and the liner subassembly described above is adhered to second side 447 of adhesive layer 442. Specifically, the application layer 434 side may be placed on and urged against the exposed adhesive of second side 447 of adhesive layer 442 such that the periphery of the liner subassembly is aligned with the periphery of the compression layer subassembly, and central apertures 428, 426, and 436 are coaxial with central apertures 444, 446. In some embodiments, perforation or slit 432 and/or pull tab 430 also may be aligned with slots 448, 450. Accordingly, adhesive subassembly 408 is completed in this embodiment.

Next, collar liner 456 may be removed to expose the adhesive on second side 422 of dressing 418. Collar 452 may be placed on and urged against the exposed adhesive to secure it in place against dressing. As will be appreciated, when this is done, central aperture 454 may be coaxial with central aperture 428.

Flange liner 458 (where provided) subsequently may be removed. In other embodiments, a single liner covering the same area as liners 456, 458 may be provided, and this will have been removed at the previous step. In any event, anchor 402 (coupled with drain tube 404) may then be coupled with the adhesive subassembly 408, and specifically with the exposed adhesive on the second side 422 of dressing 418. In particular, the end of drain tube 404 extending from body 410 may be threaded through central apertures 454, 428, 426, 436, 446, and 444, and body 410 (beginning with distal end 416) likewise may be threaded through these apertures. As this is done, flange 412 may be placed in contact with and urged against the exposed adhesive on dressing 418. When anchor 402 is coupled with adhesive assembly 408, body 410 will be received in and aligned with slots 448, 450 of adhesive subassembly 408. Thus, anchor assembly 400 (e.g., as shown in FIGS. 18-19E) may be completed in this embodiment.

As will be appreciated, when assembly is complete, collar 452 will be disposed around body 410 of anchor 402 and beneath dressing 418. Collar 452 may prevent flange 412 of anchor 402 from passing through aperture 426 in dressing 418 when external forces are applied after the anchor 402 is attached to a patient's skin. Therefore, a thinner and more flexible dressing 418 may be used in anchor assembly 400.

In accordance with another embodiment, a method of applying an anchor to a patient is provided. The method begins, and an anchor assembly 400 (such as was assembled in the previously described method) is provided. The physician may prepare the site, as appropriate, including sterilization and/or anesthetic as needed or required, and the anchor assembly 400 may be sterilized as well. Then, the insertion end of drain tube 404 may be inserted into the patient's body. Next, installation liner 424 may be removed. For example, each side thereof defined by perforation or slit 432 may be removed separately around drain tube 404, or where perforation or slit 432 is not provided, installation liner 424 may be removed by threading it around drain tube 404 prior to insertion of the insertion end of drain tube 404 into the patient's body.

In any event, the adhesive on the second side of dressing 418 may be fully exposed, and the physician may then place the adhesive second side of dressing 418 against the patient's skin. Next, the physician may apply pressure to compression layer 440 for a suitable time, such as 10-30 seconds. Via compression layer 440 and application layer 434, this force will be evenly distributed over the entire adhesive area. After the suitable time has passed, the physician may remove the compression layer 440 and the application layer 434 attached thereto via the adhesive layer 442. Specifically, the compression layer 440 is pulled, which causes the application layer 434 to separate at perforation or slit 438 and to lift off of the first surface 420 of dressing 418. In other words, application layer 434 is removed with compression layer 440. As the application layer 434 is now in two pieces, it may pass around drain tube 404. Similarly, the drain tube 404 may pass through slot 448 in compression layer 440. In embodiments where application layer 434 does not have a perforation or slit 438, application layer 434 and compression layer 440 may be threaded along drain tube 404 to be removed at the distal end thereof. Therefore, the anchor 402 remains affixed to the patient's skin via adhesive dressing 418 and collar 452, with body 410 and the distal end of drain tube 404 projecting outward from central aperture 426. The method then ends.

Based on the foregoing, it will be appreciated that embodiments of the invention provide improved apparatus and methods for anchoring a catheter to a human body. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A method of securing a catheter to a human body, the method comprising:
    providing an anchor assembly, the anchor assembly comprising:
        an anchor formed of an elastomeric first material, the anchor comprising an anchor body and a flange coupled with the anchor body, the flange having a top side and a bottom side opposite the top side, the bottom side configured to engage the human body without adhesive;
        a collar defining a central aperture and formed of a second rigid material, wherein the anchor body is received in the central aperture, the collar having a bottom side engaging the flange top side and an opposite top side;
        a dressing, the dressing having a bottom side coupled with the collar top side and the flange top side, the dressing having a top side opposite the dressing bottom side;
        an application layer releasably coupled with the dressing top side; and
        a compression layer coupled with the application layer;
    inserting at least a portion of the catheter in a passage of the human body;
    coupling at least a portion of the catheter with the anchor body;
    placing the flange bottom side against the human body, wherein the flange bottom side does not adhere to the human body;
    adhering at least a portion of the dressing to the human body;
    applying a compressive force to the compression layer; and
    removing the compression layer from the application layer.

2. The method of claim 1, wherein the compression layer is formed from a closed cell foam material.

3. The method of claim 1, wherein the application layer comprises polyethylene terephthalate.

4. The method of claim 1, wherein the collar comprises a polycarbonate material.

5. The method of claim 1, further comprising a removable liner layer coupled with the dressing bottom side.

6. A method of securing a catheter to a human body, the method comprising:
    providing an anchor assembly, the anchor assembly comprising:
        an anchor comprising an anchor body, a flange depending from the anchor body, and an internal bore extending between a distal end of the anchor body and an opening defined in the flange;
        at least one catheter coupled with the anchor and in fluid communication with the internal bore;
        an adhesive layer coupled with the flange and extending radially outward thereof, the adhesive layer having a first side adjacent the flange and a second side opposite the first side;
        a first liner layer releasably attached with the adhesive layer first side;
        a compression layer releasably coupled with the adhesive layer second side; and
        an application layer disposed between the compression layer and the adhesive layer second side;
    inserting at least a portion of the at least one catheter in a passage of the human body;
    removing the first liner layer from the anchor assembly to expose an adhesive on the first side of the adhesive layer;
    placing the flange into engagement with the human body, wherein the flange does not adhere to the human body;
    adhering the adhesive layer to the human body;
    applying a compressive force to the compression layer; and
    removing the compression layer from the adhesive layer.

* * * * *